(12) United States Patent
Christopher

(10) Patent No.: US 6,668,821 B2
(45) Date of Patent: *Dec. 30, 2003

(54) LARYNGEAL MASK AIRWAY

(75) Inventor: Kent L. Christopher, Denver, CO (US)

(73) Assignee: Evergreen Medical Incorporated, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/908,380

(22) Filed: Jul. 18, 2001

(65) Prior Publication Data

US 2001/0050082 A1 Dec. 13, 2001

Related U.S. Application Data

(63) Continuation-in-part of application No. 09/840,194, filed on Apr. 23, 2001, application No. 09/908,380, and a continuation-in-part of application No. 09/767,272, filed on Jan. 22, 2001, which is a continuation-in-part of application No. 09/707,350, filed on Nov. 6, 2000, which is a continuation-in-part of application No. 09/411,610, filed on Oct. 1, 1999, which is a continuation-in-part of application No. 08/974,864, filed on Nov. 20, 1997, now Pat. No. 5,964,217, which is a continuation of application No. 08/607,332, filed on Feb. 26, 1996, now Pat. No. 5,694,929.

(60) Provisional application No. 60/252,347, filed on Nov. 20, 2000.

(51) Int. Cl.[7] ............................................. A61M 16/00

(52) U.S. Cl. ........................ 128/200.26; 128/207.14; 128/207.15

(58) Field of Search ................. 128/200.26, 207.14, 128/207.15

(56) References Cited

U.S. PATENT DOCUMENTS

| | | | | |
|---|---|---|---|---|
| 4,240,417 A | | 12/1980 | Holever | |
| 4,327,720 A | | 5/1982 | Bronson et al. | |
| 4,351,328 A | | 9/1982 | Bodai | |
| 4,416,273 A | | 11/1983 | Grimes | |
| 4,497,318 A | * | 2/1985 | Donmichael | 128/202.28 |
| 4,509,514 A | | 4/1985 | Brain | |
| 4,832,020 A | * | 5/1989 | Augustine | 128/207.14 |
| 4,848,331 A | | 7/1989 | Northway-Meyer | |
| 4,892,095 A | | 1/1990 | Nakhgevany | |
| 4,995,388 A | | 2/1991 | Brain | |
| 5,038,766 A | * | 8/1991 | Parker | 128/200.26 |
| 5,174,283 A | * | 12/1992 | Parker | 128/200.26 |
| 5,197,463 A | * | 3/1993 | Jeshuran | 128/207.14 |
| 5,241,956 A | | 9/1993 | Brain | |
| 5,249,571 A | | 10/1993 | Brain | |
| 5,282,464 A | | 2/1994 | Brain | |
| 5,297,547 A | | 3/1994 | Brain | |
| 5,303,697 A | | 4/1994 | Brain | |
| 5,305,743 A | | 4/1994 | Brain | |
| 5,339,805 A | * | 8/1994 | Parker | 128/200.26 |
| 5,339,808 A | * | 8/1994 | Don Michael | 128/207.15 |
| 5,355,879 A | | 10/1994 | Brain | |
| 5,391,248 A | | 2/1995 | Brain | |
| 5,584,290 A | | 12/1996 | Brain | |
| 5,632,271 A | | 5/1997 | Brain | |
| 5,642,726 A | | 7/1997 | Owens et al. | |
| 5,682,880 A | * | 11/1997 | Brain | 128/207.15 |

(List continued on next page.)

Primary Examiner—Weilun Lo
Assistant Examiner—Joseph F. Weiss, Jr.
(74) Attorney, Agent, or Firm—Dorr, Carson, Sloan & Birney, P.C.

(57) ABSTRACT

A laryngeal mask airway has a curved tubular guide for insertion through the patient's mouth and oropharynx. After insertion of the guide, the beveled distal opening of the guide abuts the laryngeal inlet, while the guide's proximal opening remains outside the patient's mouth. A laryngeal mask surrounds the distal opening of the guide to substantially seal the laryngeal inlet about the distal opening of the guide A ventilation port adjacent to the proximal opening of the guide supplies air/oxygen through the guide into the patient's lungs. An endotracheal tube can then be advanced along the length of guide and through the patient's larynx without interrupting ventilation.

20 Claims, 20 Drawing Sheets

U.S. PATENT DOCUMENTS

| | | | | |
|---|---|---|---|---|
| 5,694,929 A | * | 12/1997 | Christopher | 128/207.14 |
| 5,711,293 A | | 1/1998 | Brain | |
| 5,720,275 A | | 2/1998 | Patil et al. | |
| 5,771,889 A | | 6/1998 | Pagan | |
| 5,871,012 A | | 2/1999 | Neame et al. | |
| 5,878,745 A | | 3/1999 | Brain | |
| 5,881,726 A | | 3/1999 | Neame | |
| 5,890,488 A | | 4/1999 | Burden | |
| 5,896,858 A | | 4/1999 | Brain | |
| 5,937,860 A | | 8/1999 | Cook | |
| 5,964,217 A | * | 10/1999 | Christopher | 128/200.26 |
| 5,979,445 A | | 11/1999 | Neame et al. | |
| 5,983,897 A | | 11/1999 | Pagan | |
| 6,003,514 A | * | 12/1999 | Pagan | 128/207.15 |
| 6,012,452 A | | 1/2000 | Pagan | |
| 6,050,264 A | | 4/2000 | Greenfield | |
| 6,055,984 A | | 5/2000 | Brain | |
| 6,079,409 A | | 6/2000 | Brain | |
| 6,116,243 A | | 9/2000 | Pagan | |
| 6,119,695 A | | 9/2000 | Augustine et al. | |

* cited by examiner

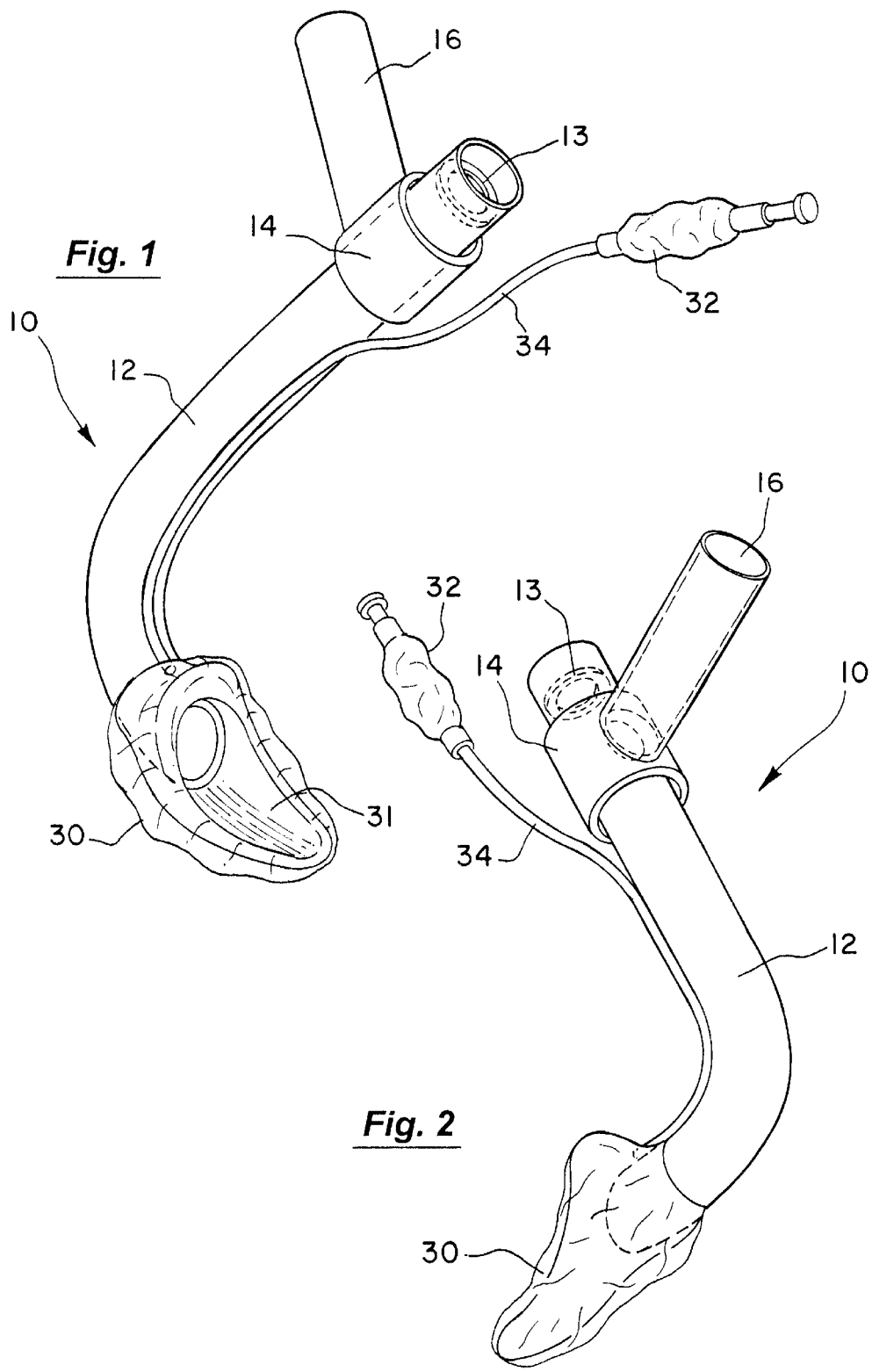

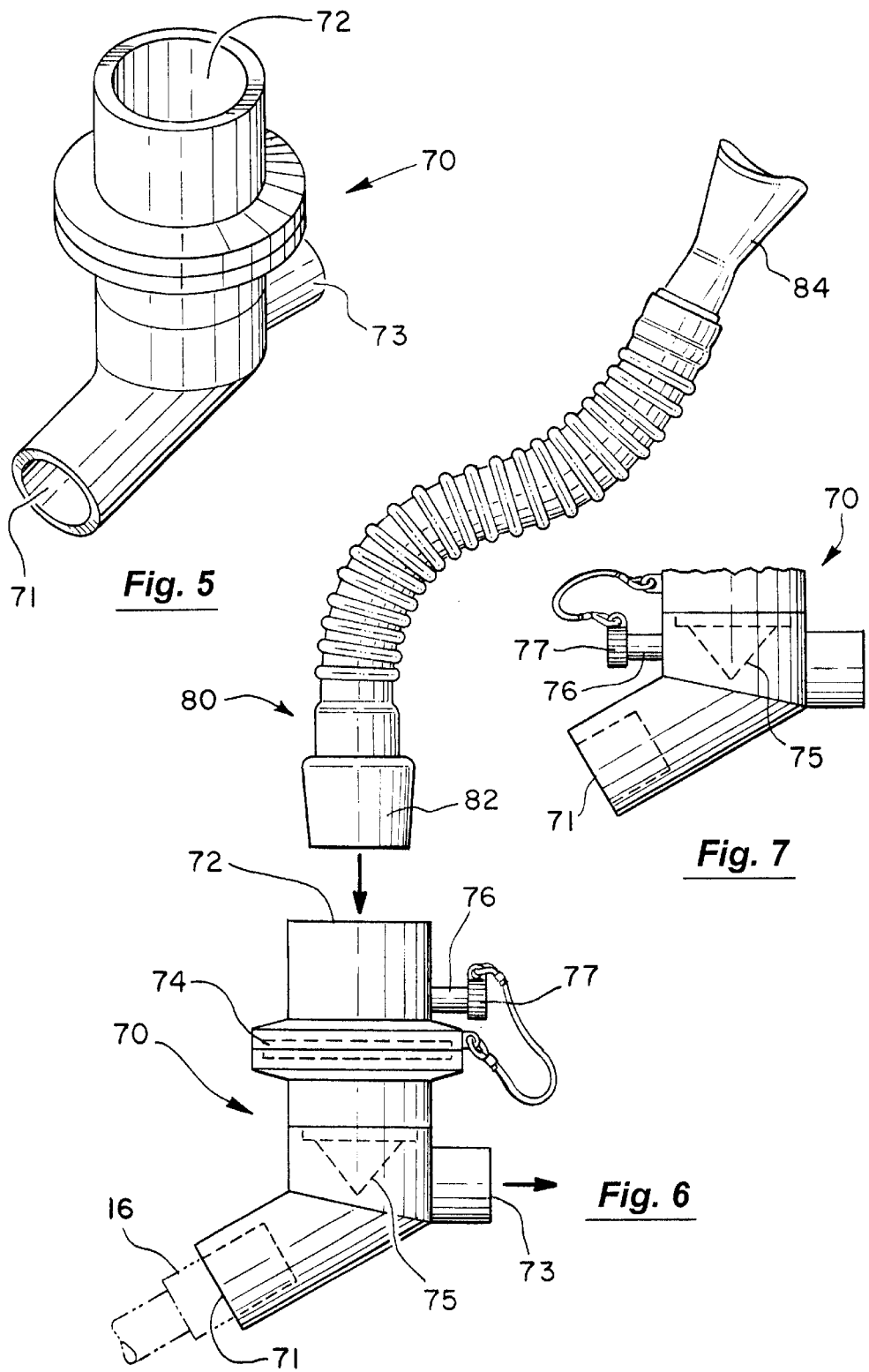

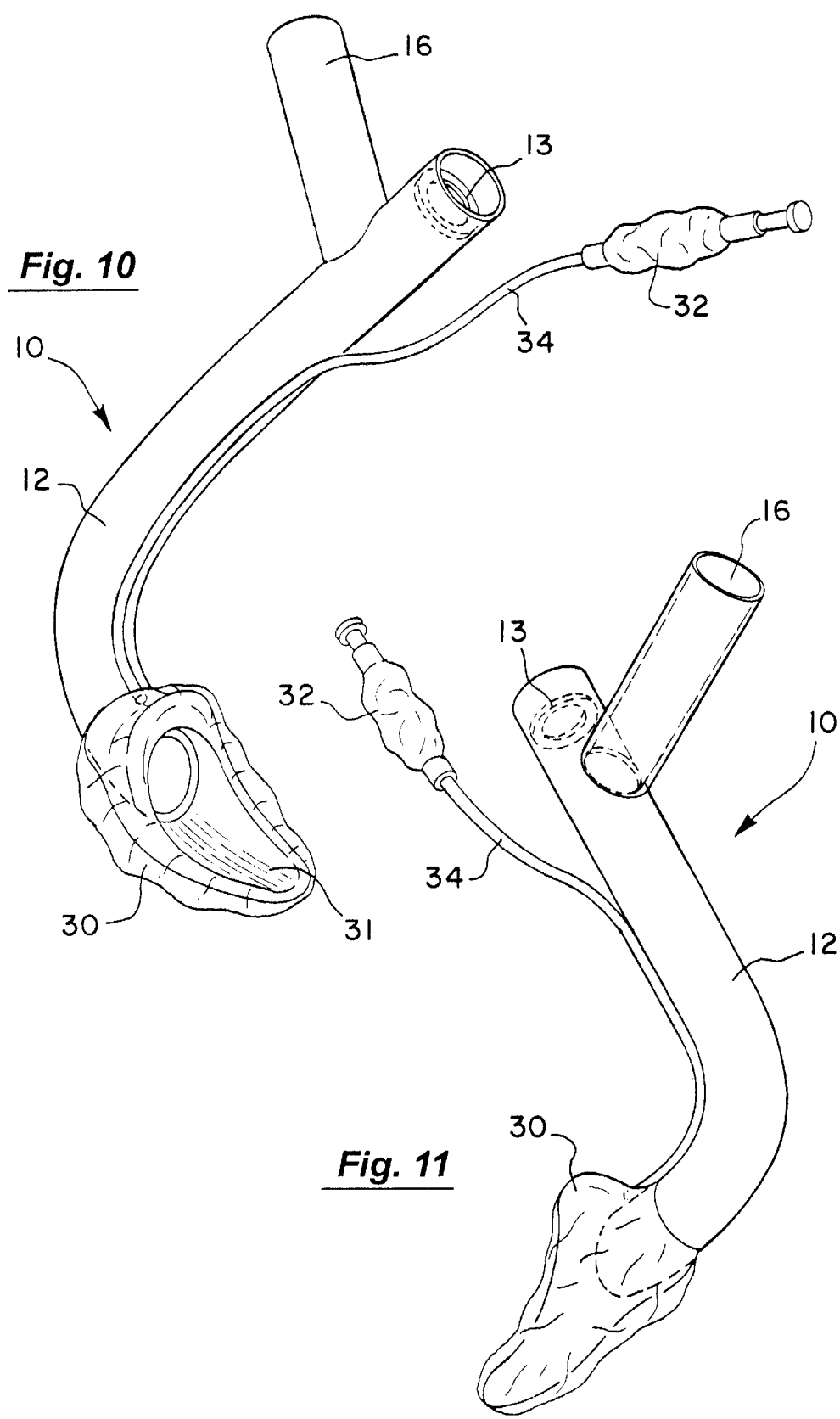

*Fig. 22*
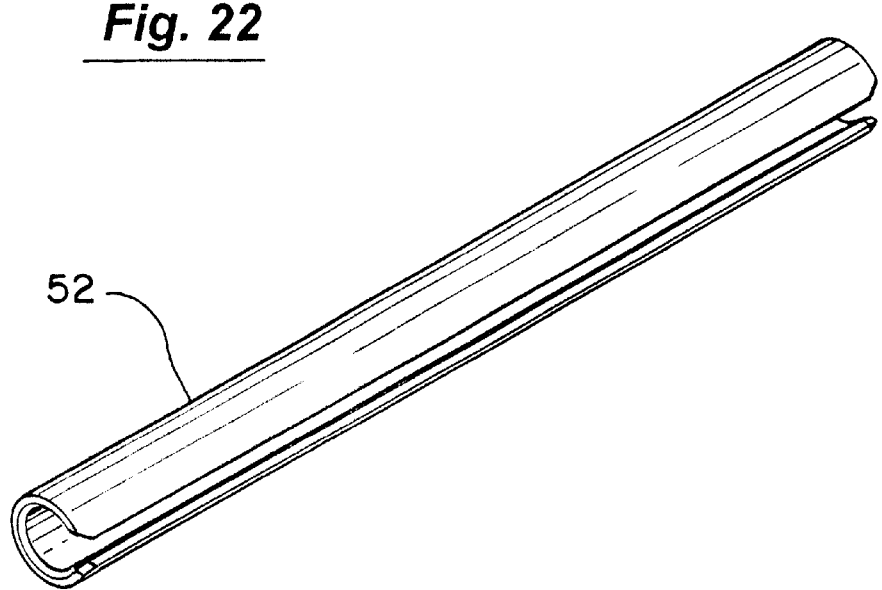
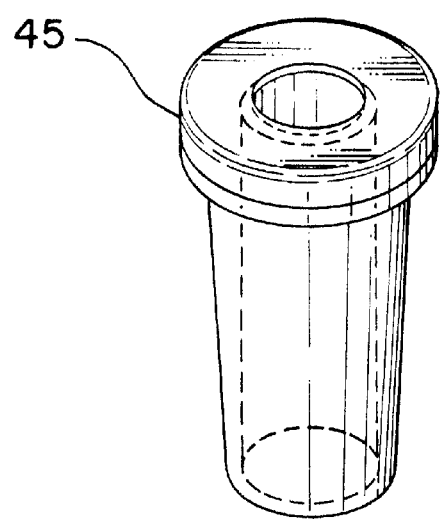
*Fig. 23*

LARYNGEAL MASK AIRWAY

RELATED APPLICATIONS

The present application is a continuation-in-part of the Application's co-pending U.S. patent application Ser. No. 09/840,194, entitled "Laryngeal Mask Airway," filed on Apr. 23, 2001, which claims priority to U.S. Provisional Patent Application Ser. No. 60/252,347, filed on Nov. 20, 2000. The present application is also a continuation-in-part of the Applicant's co-pending U.S. patent application Ser. No. 09/767,272, entitled "Method and Apparatus for Ventilation/ Oxygenation During Guided Insertion of an Endotracheal Tube," filed on Jan. 22, 2001, which is a continuation-in-part of U.S. patent application Ser. No. 09/707,350, filed on Nov. 6, 2000, which is a continuation-in-part of U.S. patent application Ser. No. 09/411,610, filed on Oct. 1, 1999, which is a continuation-in-part of U.S. patent application Ser. No. 08/974,864, filed on Nov. 20, 1997, now U.S. Pat. No. 5,964,217, issued on Oct. 12, 1999, which is a continuation of U.S. patent application Ser. No. 08/607,332, filed on Feb. 26, 1996, now U.S. Pat. No. 5,694,929, issued on Dec. 9, 1997.

BACKGROUND OF THE INVENTION

1. Field of the Invention

The present invention relates generally to the field of laryngeal mask airways. More specifically, the present invention discloses an intubation guide and laryngeal mask that can be used to simultaneously intubate and ventilate a patient.

2. Background of the Invention

Endotracheal tubes are often used in semi-emergency situations to ventilate patients with respiratory failure who may be conscious or semi-conscious. The conventional approach requires the patient to lie still while the physician inserts a rigid laryngoscope blade into the patient's mouth and trachea. Delivery of ventilation and/or oxygen is also interrupted during this period. The endotracheal tube is then inserted into place while the laryngoscope blade keeps the patient's airway open. Successful intubation depends on the patient being cooperative and completely relaxed, which unfortunately is often not the case. Even with a cooperative patient, intubation is very uncomfortable and can cause the patient to panic due to the difficulty in breathing during the procedure. This procedure can also result in a choking or gagging response that can cause the patient to regurgitate and aspirate contents from the stomach. One conventional response to these shortcomings has been to sedate the patient during intubation. Tranquilizers make the patient more cooperative and less likely to choke during intubation, but also tend to suppress the patient's breathing and blood pressure. These side effects may be unacceptable when dealing with a patient who already suffers from shallow or irregular breathing or depressed blood pressure. Therefore, a need exists for an improved device to guide insertion of an endotracheal tube and ensure that the patient's airway is open, and that also allows the patient to continue to receive air/oxygen during the insertion process.

Laryngeal masks have also been used for many years for several purposes. For example, laryngeal mask airways have been used to ventilate patients while preventing aspiration of secretions or stomach contents into the lungs. Some types of intubation guides include a laryngeal mask to seal the laryngeal inlet while directing the endotracheal tube into position through the larynx.

Prior Art. The prior art in the field includes the following:

| U.S. Pat. No. | Inventor |
| --- | --- |
| 4,240,417 | Holever |
| 4,351,328 | Bodai |
| 4,416,273 | Grimes |
| 4,509,514 | Brain |
| 4,848,331 | Northway-Meyer |
| 4,995,388 | Brain |
| 5,197,463 | Jeshuran |
| 5,241,956 | Brain |
| 5,249,571 | Brain |
| 5,282,464 | Brain |
| 5,297,547 | Brain |
| 5,303,697 | Brain |
| 5,305,743 | Brain |
| 5,391,248 | Brain |
| 5,355,879 | Brain |
| 5,584,290 | Brain |
| 5,632,271 | Brain |
| 5,642,726 | Owens et al. |
| 5,682,880 | Brain |
| 5,711,293 | Brain |
| 5,771,889 | Pagan |
| 5,871,012 | Neame et al. |
| 5,878,745 | Brain |
| 5,881,726 | Neame et al. |
| 5,890,488 | Burden |
| 5,896,858 | Brain |
| 5,937,860 | Cook |
| 5,979,445 | Neame et al. |
| 5,983,897 | Pagan |
| 6,012,452 | Pagan |
| 6,050,264 | Greenfield |
| 6,055,984 | Brain |
| 6,079,409 | Brain |
| 6,116,243 | Pagan |

Holever discloses an adaptor to connect a ventilator to an endotracheal tube, while also permitting insertion of a suction tube.

Bodai discloses a system for simultaneous ventilation and endotracheal suctioning of a patient.

Grimes discloses a connector valve assembly for endotracheal tubes.

The Brain '514 patent discloses a laryngeal mask with a generally elliptical shape and a guide tube.

Northway-Meyer discloses a face mask and intubation guide, which includes a connector for ventilation through the face mask and intubation guide.

Brain '388 patent discloses a laryngeal mask with a soft flexible collar surrounding the lumen of the mask, and also having a drainage tube.

Jeshuran discloses a face mask and adaptor for endotracheal intubation.

The Brain '956 patent discloses a laryngeal mask airway with concentric drainage for esophageal discharge.

The Brain '571 patent discloses a laryngeal clamp airway.

The Brain '464 patent discloses a combined laryngeal mask and reflectance oximeter.

The Brain '547 patent discloses a laryngeal mask with an inflatable cuff and a V-shaped posterior side.

The Brain '697 patent discloses a laryngeal mask with a rigid handle at the proximal end of the guide tube.

The Brain '743 and '248 patents disclose a molding process for producing laryngeal masks.

The Brain '879 patent discloses a laryngeal mask with inflatable ring and inflatable back cushion.

The Brain '290 patent discloses a laryngeal mask with electrodes.

The Brain '271 patent discloses a laryngeal mask with a gastric drainage feature.

The Brain '880 patent discloses a laryngeal mask with a removable stiffener that can be attached to the guide.

The Brain '293 patent discloses a forming tool for deflating a laryngeal mask, such as that shown in the Brain '547 patent, prior to insertion.

The Pagan '889 patent discloses a mask assembly having an inflatable ring and a diaphragm attached to a backing plate.

The '012 patent to Neame et al. discloses a laryngeal mask with an inflatable bag.

The Brain '745 patent discloses a gastro-laryngeal mask with an inflatable cuff and a back cushion to engage the back wall of the pharynx.

The '726 patent to Neame et al. discloses a laryngeal mask with a cuff formed by interlocking ribs.

Burden discloses a coupling device for placing a stethoscope and an endotracheal tube in gaseous communication.

The Brain '858 patent discloses a laryngeal mask with a hinged bar to elevate the epiglottis.

Cook discloses a laryngeal mask with an inflatable toroidal peripheral portion having a recessed front notch.

The '445 patent to Neame et al. discloses a method for manufacture of a laryngeal mask in which the edges of the cuff are heat-sealed.

The Pagan '897 patent discloses a laryngeal mask with cuffs attached on both sides of a plate. The plate also forms a leading tip.

The Pagan '452 patent discloses a laryngeal mask with an air line extending to a foam cuff. The cuff can be compressed for insertion by applying suction to the air line.

Greenfield discloses a laryngeal mask requiring an obdurator inserted into the tube.

The Brain '984 patent discloses an endotracheal tube having tapered, closed nose with a triangular cross-section and lateral openings.

The Brain '409 patent discloses a laryngeal mask having a specific geometry for the guide tube and mask.

The Pagan '243 patent discloses a laryngeal mask with a plate separating two separate semi-annular cuffs bonded to opposite sides of the plate.

Solution to the Problem. None of the prior art references discussed above teaches or suggests a laryngeal mask airway that enables the patient to continue to be ventilated while being intubated. This system allows the endotracheal tube to be inserted and connected to a ventilator without interrupting the flow of air/oxygen to the patient's lungs.

SUMMARY OF THE INVENTION

This invention provides a laryngeal mask airway having a curved tubular guide for insertion through the patient's mouth and oropharynx. After insertion of the guide, the beveled distal opening of the guide abuts the laryngeal inlet, while the guide's proximal opening remains outside the patient's mouth. A laryngeal mask surrounds the distal opening of the guide to substantially seal the laryngeal inlet about the distal opening of the guide. A ventilation port adjacent to the proximal opening of the guide supplies a flow of air/oxygen through the guide into the patient's lungs. An endotracheal tube can then be advanced along the length of guide and through the patient's larynx without interrupting ventilation.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 1 is a front perspective view of a laryngeal mask airway 10 with a rotatable collar 14 for delivery of air/oxygen through the guide 12.

FIG. 2 is rear perspective view of the laryngeal mask airway corresponding to FIG. 1.

FIG. 5 is a perspective view of a resuscitation attachment 70 that can be connected to the ventilation port 16 of the laryngeal mask airway 10.

FIG. 6 is a corresponding side view of the resuscitation attachment 70 with flexible tubing 80 having a mouthpiece 84 for resuscitation of the patient.

FIG. 7 is a detail side view of an embodiment of the resuscitation attachment 70 having an oxygen port 76.

FIG. 10 is a front perspective view of another embodiment of the laryngeal mask airway 10 in which the ventilation port 16 is fixed relative to the guide 12.

FIG. 11 is a rear perspective view of the laryngeal mask airway 10 corresponding to FIG. 10.

FIG. 22 is a perspective view of the stabilizer 52 that can be attached to an endoscope probe 50 to advance the endotracheal tube 40 along the laryngeal mask airway 10

FIG. 23 is a perspective view of the endotracheal tube cap 45 that can be used in conjunction with a stabilizer 52 to advance the endotracheal tube 40.

DETAILED DESCRIPTION OF THE INVENTION

Figure 3:
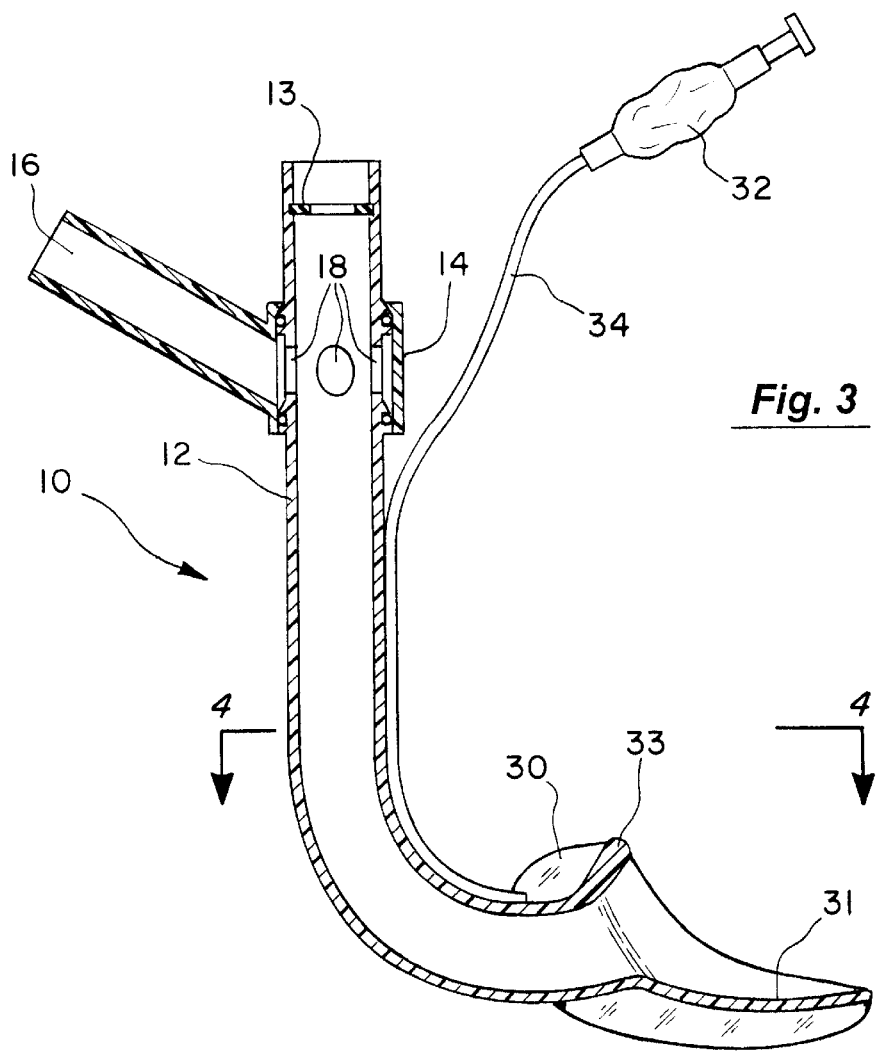
FIG. 3 is a cross-sectional view of the laryngeal mask airway 10 corresponding to FIG. 1 with the mask 30 inflated.
Figure 4:
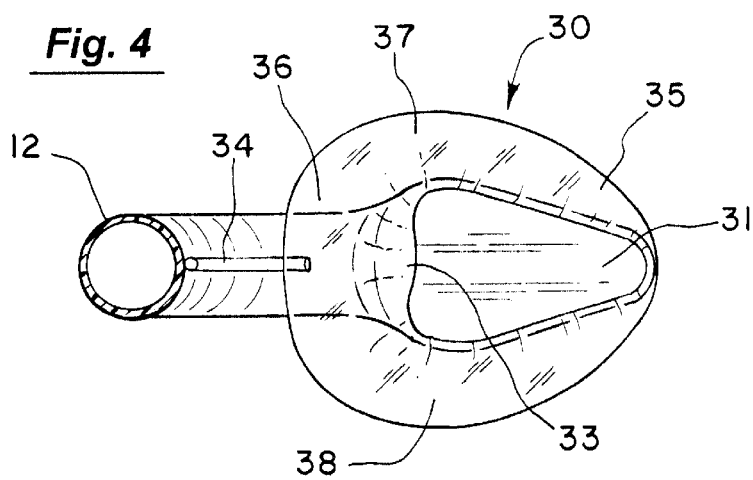
FIG. 4 is a detail cross-sectional view of the distal portion of the laryngeal mask airway 10.

Structure of the Laryngeal Mask Airway. Turning to FIGS. 1 and 2, front and rear perspective views are provided of a laryngeal mask airway 10 in accordance with the present invention. This embodiment includes a tubular guide 12 with a laryngeal mask 30 surrounding its distal end. FIG. 3 is a corresponding cross-sectional view of the laryngeal mask airway 10 with the laryngeal mask 30 inflated. FIG. 4 is a detail end view of the laryngeal mask 30 and the distal portion of the guide 12. The size and shape of the guide 12 are selected so that its distal portion can be readily inserted into the patient's mouth and upper airway with the laryngeal mask 30 substantially sealing the laryngeal inlet 27, as shown in FIGS. 14–18. The proximal end of the guide 12 remains outside of the patient's mouth and therefore is accessible to the healthcare provider.

Figure 13:
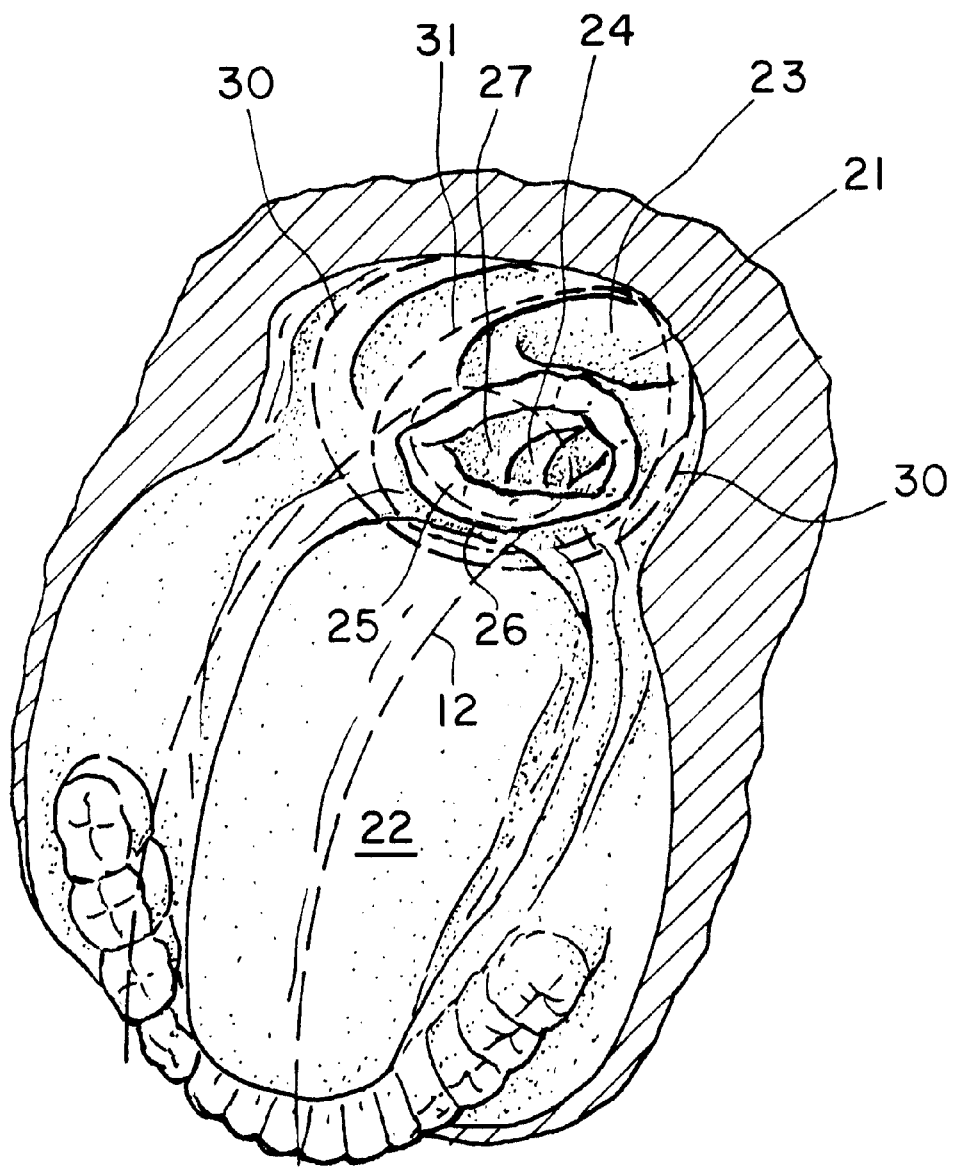
FIG. 13 is a top perspective view of a patient's airway showing the inlet to the larynx, esophagus, and epiglottis.
Figure 14:
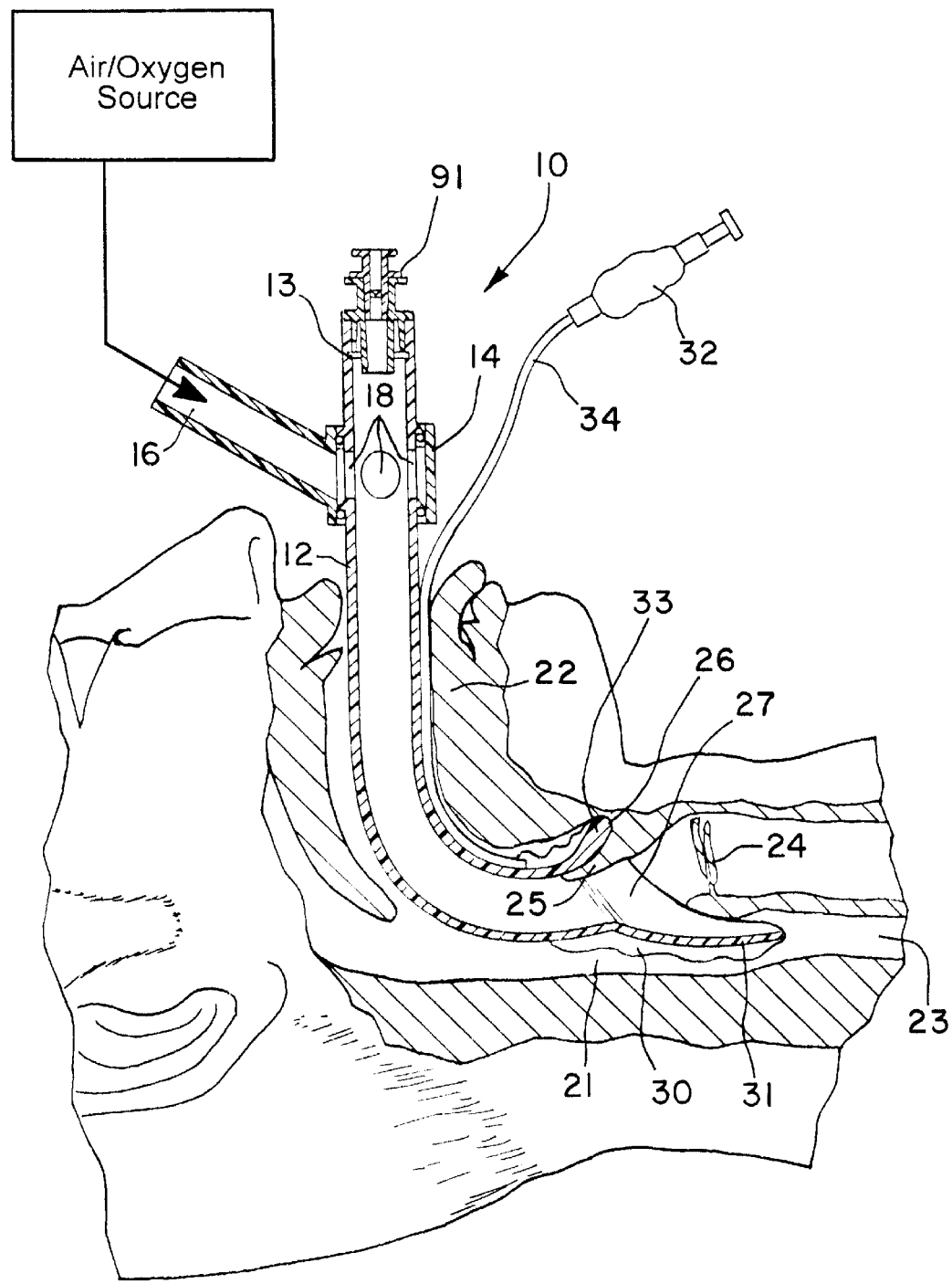
FIG. 14 is a cross-sectional view of a patient's airway after the laryngeal mask airway 10 has been initially inserted.

The guide 12 is generally J-shaped to follow the profile of a typical patient's airway through the mouth, over the tongue 22, and into the laryngopharynx 21 just above the opening to the larynx 24 (see FIGS. 13 and 14). The guide 12 is shaped to prevent the patient's tongue 22 and collapsible pharynx from obstructing access to the trachea, while also defining a channel for later insertion of an endotracheal tube. The guide 12 is typically made of plastic with sufficient strength and rigidity to keep the patient's teeth apart and prevent the patient from biting down on the endotracheal tube. This flexibility allows the guide 12 to accommodate a wide range of patient sizes and conditions. The inside diameter of the guide 12 should be sufficiently large to allow an endotracheal tube 40 to freely pass through the guide 12, as shown for example in FIG. 17, with extra room to allow air/oxygen to flow through the guide 12 around the endotracheal tube 40. Preferably, the distal opening of the guide 12 is beveled to substantially match the angle of the laryngeal inlet 27 after insertion of the laryngeal mask airway 10 into the patient's airway.

The laryngeal mask 30 consists a central support member 31 extending outward from the guide 12 to an inflatable member as illustrated in FIGS. 1–4. The laryngeal mask 30 is preferably made of a soft, flexible material (e.g., a polymer or rubber) to enable it to be advanced into position without injury to the patient and to create a substantially air-tight seal about the laryngeal inlet 27. The degree of inflation of the laryngeal mask 30 can be adjusted through a small inflation tube 34 and air valve 32. Alternatively, the laryngeal mask 30 can be a cushion made of a soft, spongy material that is not inflatable. The laryngeal mask 30 and its support member 31 are shaped to meet several requirements. The lower portion 35 of the laryngeal mask 30 substantially blocks the esophagus to minimize the risk of regurgitation of stomach contents and the passage of air into the stomach. The upper portion 36 of the laryngeal mask 30 guides the distal end of the guide 12 into alignment with the laryngeal inlet 27 as the guide is inserted along the patient's airway.

In the embodiment shown in the drawings, the laryngeal mask 30 is generally boot-shaped when inflated. The lower portion 35 of the laryngeal mask 30 forms the toe of the boot, which blocks the esophagus. The lower portion 35 of the laryngeal mask 30 also helps to align the distal opening of the guide 12 with the patient's laryngeal inlet 27. After the mask 30 is inflated, the upper portion 36 of the mask 30 substantially fills the laryngopharynx 21 at the level of the laryngeal inlet 27. The upper portion 36 of the laryngeal mask 30 surrounds the laryngeal inlet 27 so that the distal opening of the guide 12 is sealed in fluid communication with the laryngeal inlet 27. Thus, substantially all of the gas inhaled or exhaled by the patient passes through the guide 12. For example, the laryngeal mask 30 can be formed by injection blow molding, rotational molding, or dip molding.

In particular, the upper portion 36 of the mask 30 surrounding the distal opening of the guide 12 is canted at an angle to complement the natural angle of the laryngeal inlet 27. The distal end of the guide 12 can also be beveled at this complementary angle. This enables the laryngeal mask airway 10 to directly engage the laryngeal inlet 27 along the longitudinal axis of the patient's airway as the guide 12 is advanced. The shape of the upper portion 36 of the laryngeal mask 30 further helps to guide the distal opening of the guide 12 so that it is axially aligned with the laryngeal inlet 27 and abuts the laryngeal inlet 27 in an end-on relationship as the guide is inserted along the patient's airway. In contrast, conventional laryngeal masks typically approach the laryngeal inlet 27 from a posterior or inferior position.

Figure 8:
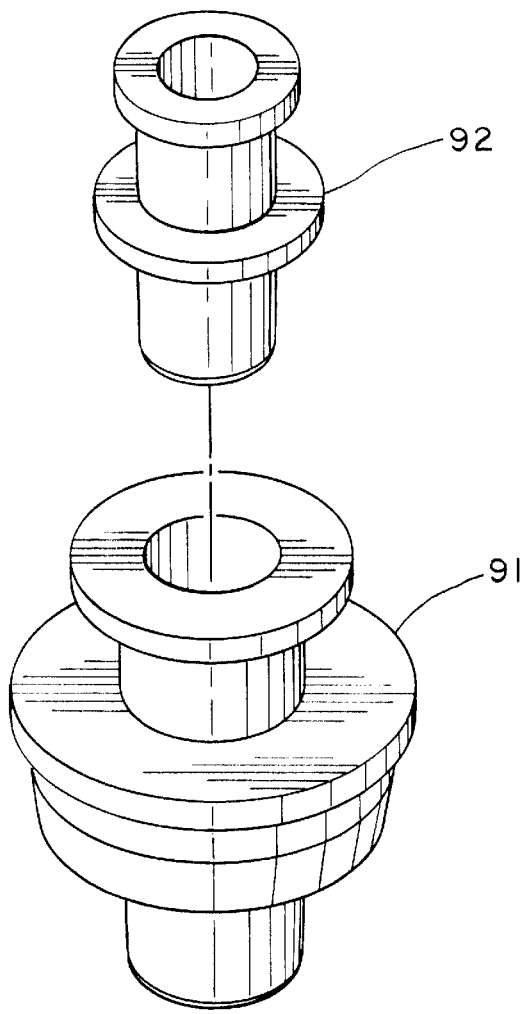
FIG. 8 is an exploded perspective view of the removable guide cap 91 that can be inserted into the proximal opening of the guide 12 of the laryngeal mask airway 10.
Figure 9:
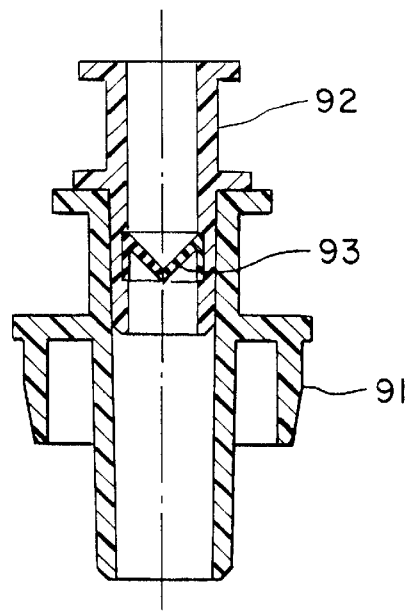
FIG. 9 is a cross-sectional view of the removable guide cap 91 corresponding to FIG. 8.

In the embodiment depicted in FIGS. 1–4, the proximal end of the guide 12 can be sealed by a removable guide cap 91 as shown in FIG. 8, 9, and 14. FIG. 8 is an exploded perspective view of the guide cap 91, while FIG. 9 is provides a cross-sectional view of the guide cap 91. FIG. 14 is a cross-sectional view of a patient's airway after the laryngeal mask airway 10 has been initially inserted. As shown in FIG. 14, the guide cap 91 has an outside diameter dimensioned to seat into the proximal opening of the guide 12 and thereby prevent the escape of gas through this opening. When inserted, the guide cap 91 abuts and seals against an annular seal ring 13 within the guide 12 as illustrated in FIG. 14. The guide cap 91 has a small passageway or port extending vertically through the guide cap 91. As shown in FIG. 9, a luer connector 92 with a one-way valve 93 (e.g., a duck-bill valve) is permanently attached to the guide cap 91 so that air or fluid can only flow down the passageway of the guide cap 91, but not up. Thus, the one-way valve 93 serves to prevent air/oxygen from escaping through the guide 12 during resuscitation.

Figure 16:
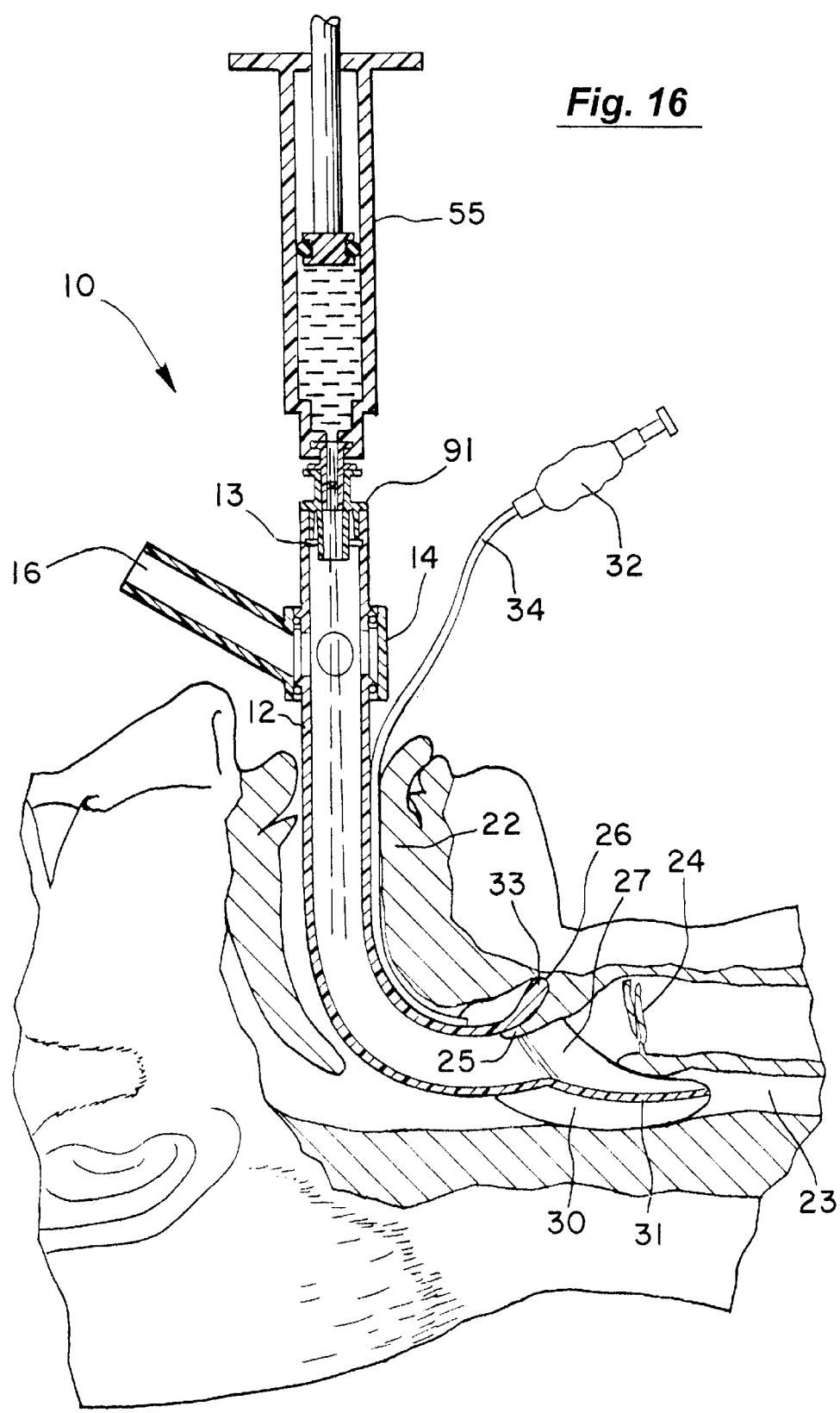
FIG. 16 is a cross-sectional view of the patient's airway and laryngeal mask airway 10 corresponding to FIGS. 14–15 showing a syringe 55 connected to the guide cap 91 on the laryngeal mask airway 10 to squirt anesthetic through the laryngeal mask airway 10 and into the patient's airway to lessen discomfort.

As illustrated in FIG. 16, a syringe 55 containing anesthetic can be secured to the luer connector 92 on the guide cap 91. As the guide 12 is advanced into the patient's mouth and hypopharynx, the healthcare provider squirts anesthetic from the syringe 55, through the one-way valve 93 and guide 12 to lessen discomfort. After the guide 12 has been advanced into position, the guide cap 91 is removed from the guide 12 to allow insertion of an endotracheal tube 40 and fiber optic probe 50 through the guide 12, as will be discussed below.

A flow of air/oxygen is delivery to the patient via the guide 12 through a ventilation port 16 extending at an angle from the side of the guide 12. A rotatable collar 14 allows the ventilation port 16 to be rotated about the central axis of the guide 12 to any desired orientation. Air/oxygen flows through the ventilating port 16 into the annular space between the collar 14 and the guide 12, and through a series of ventilation holes 18 into the interior of the guide 12, as shown in greater detail in FIG. 3. For example, the ventilation port 16 can be connected to a conventional ventilator or a resuscitation bag.

Resuscitation Attachment. Alternatively, a mouthpiece can be connected to the ventilation port 16 for initial patient resuscitation by a healthcare provider. For example, FIG. 5 is a perspective view of a resuscitation attachment 70 that can used in place of a ventilator or resuscitation bag for resuscitation by the healthcare provider. The resuscitation attachment 70 has an output port 71 that can be removably connected to the ventilation port 16 of the laryngeal mask airway 10. The resuscitation attachment 70 includes an air filter 74 across the flow path between the input port 72 and output port 71 to help prevent the exchange of contaminants between the healthcare provider and patient. A one-way valve 75 (e.g., a duckbill valve) directs any backflow of air or contaminated fluids from the patient to the exhaust port 73, and thereby serves to further protect the healthcare provider from contaminants.

The healthcare provider can breathe directly into the input port 72 of the resuscitation attachment 70. Alternatively, a length of flexible tubing 80 can be connected to the resuscitation attachment 70 by means of a connector 82 that can be plugged into the input port 72 of the resuscitation attachment 70, as shown in FIG. 6. In the preferred embodiment, the flexible tubing 80 is approximately six inches in length and forms a helical coil for easier storage. The proximal end of the flexible tubing 80 has a mouthpiece 84 with an oval opening.

The resuscitation attachment 70 can also be equipped with an oxygen port 76, as shown in FIG. 7, that can be connected by tubing to a external oxygen source to supply supplemental oxygen to the patient through the flow path, in addition to the resuscitation provided by the healthcare provider. Each exhalation by the healthcare provider then carries oxygen-enriched air through the laryngeal mask airway 10 and into the patient's lungs. The oxygen port 76 can be closed with a removable cap 77 when the oxygen port 76 is not in use. The internal passageway within the flexible tubing 80 and resuscitation attachment 70 upstream from the one-way valve 75 serve as a reservoir for accumulation of oxygen between each exhalation by the healthcare provider.

FIG. 7 shows an embodiment of the resuscitation attachment 70 with the oxygen port 76 placed below the one-way valve 75 and filter 74. In this embodiment, the internal passageway within the resuscitation attachment 70 downstream from the one-way valve 75 serves as a reservoir for accumulation of oxygen between each exhalation by the healthcare provider. The one-way valve 75 helps to prevent oxygen from escaping during the remainder of the resuscitation cycle. However, the exhaust port 73 prevents a build-up of excessive pressure that might be injurious to the patient's lungs.

FIGS. 10 and 11 are front and rear perspective views of another embodiment of the laryngeal mask airway 10 in which air/oxygen is introduced directly into the guide 12 through a fixed ventilation port 16. This embodiment would be simpler and less expensive to build.

Figure 12:
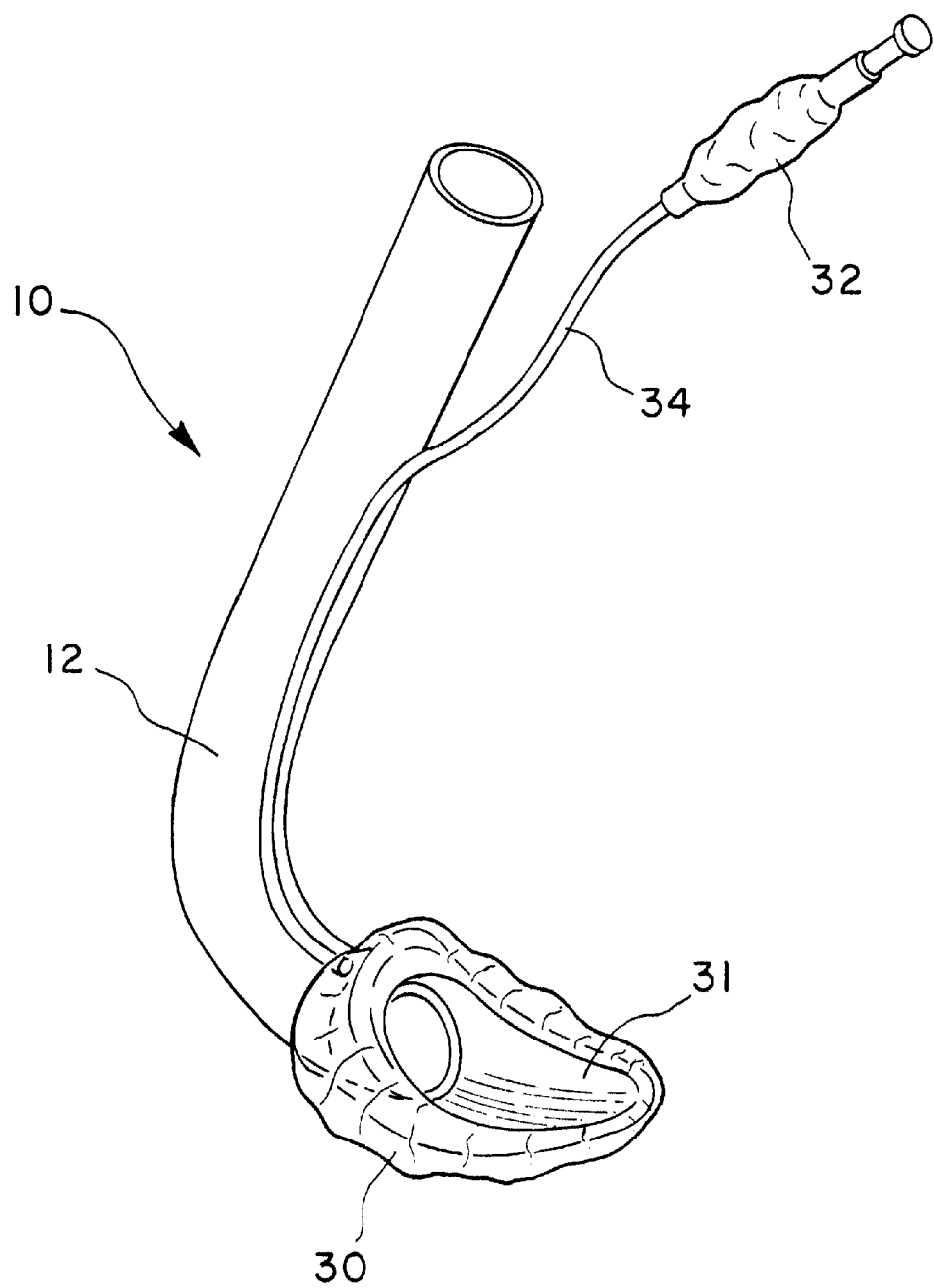
FIG. 12 is a front perspective view of another embodiment of the laryngeal mask airway without a ventilation port.

FIG. 12 is a front perspective view of yet another embodiment of the laryngeal mask airway 10 without a separate ventilation port. The patient can be supplied with air/oxygen through a connector or cap placed in the proximal opening of the guide 12. Alternatively, the patient can be intubated without ventilation.

Method Of Use For The Laryngeal Mask Airway. The following is a description of a typical method of use for the laryngeal mask airway 10.

The curved distal portion of the guide 12 is first inserted into the patient's mouth and laryngopharynx 21 with the laryngeal mask 30 deflated, as shown in FIG. 14. If necessary, the ventilation port 16 can be used as a hand grip during insertion of the guide 12. FIG. 13 is a corresponding top perspective view of a patient's airway, including the larynx 24, esophagus 23, and epiglottis 25. The positions of the guide 12 and laryngeal mask 30 relative to the patient's anatomy after insertion are shown in dashed lines in FIG. 13. The lower portions of the support member 31 and laryngeal mask 30 extend into the esophagus 23. The upper portions of the support member 31 and the laryngeal mask 30 surround the laryngeal inlet 27.

A protrusion 33 on the anterior portion of the distal tip of the guide 12 or support member 31 is inserted to the patient's vallecula 26 (i.e., the notch between the base of the tongue 22 and the epiglottis 25. The protrusion 33 pushes on the vallecula 26, which tends to lift the epiglottis 25 from the laryngeal inlet 27 and helps to ensure patency of the patient's airway.

Figure 15:
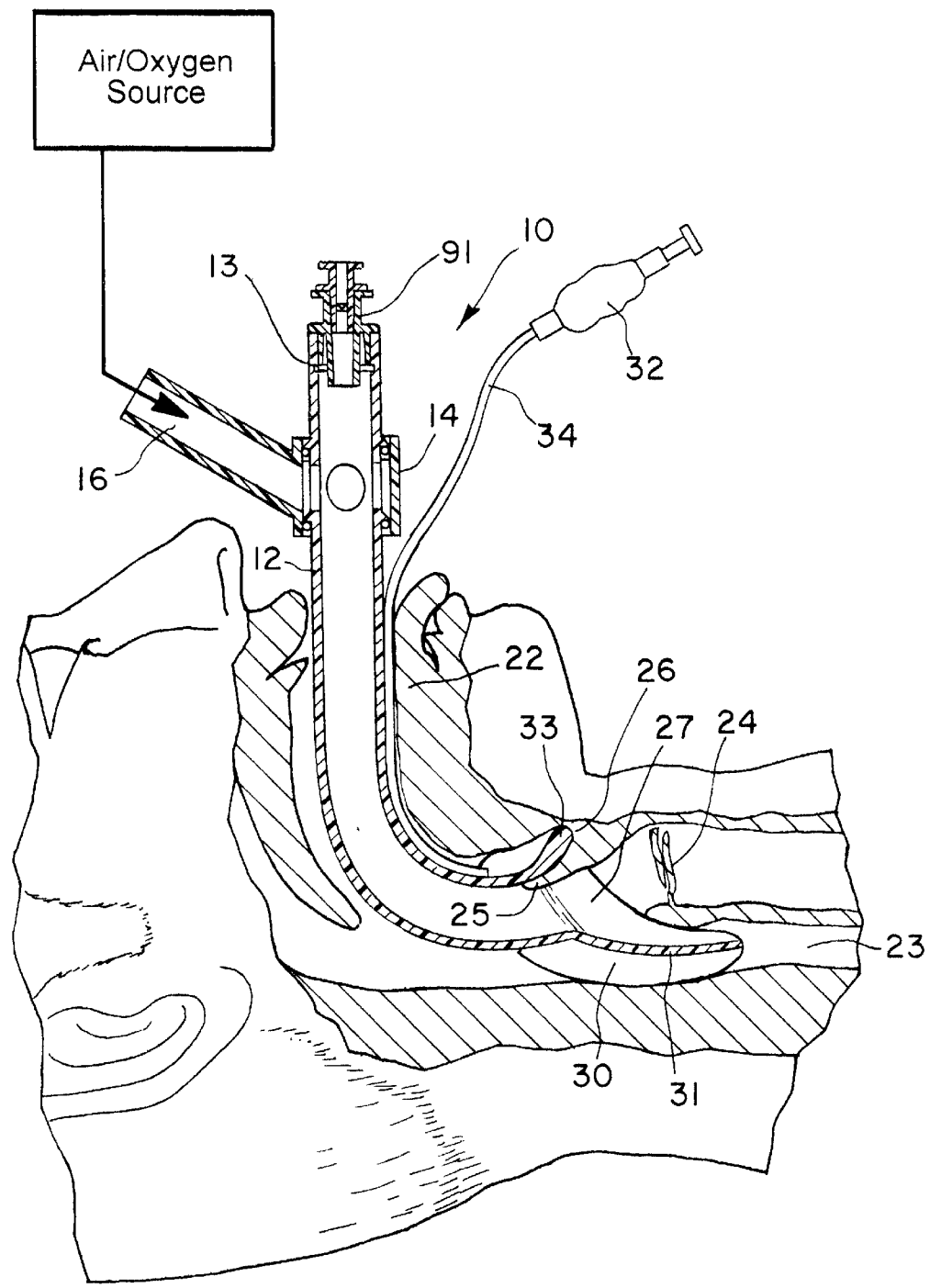
FIG. 15 is a cross-sectional view of the laryngeal mask airway 10 and the patient's airway corresponding to FIG. 14 after the mask 30 has been inflated.

After the distal portion of the guide 12 and the laryngeal mask 30 are appropriately positioned relative to the laryngeal inlet 27, the laryngeal mask 30 is inflated via the inflation tube 34 to establish a seal around the laryngeal inlet 27, as depicted in FIG. 15. The lower portion 35 of the inflated laryngeal mask 30 substantially blocks the esophagus 23. The upper portion 36 of the inflated laryngeal mask 30 substantially fills the laryngopharynx 21 adjacent to the laryngeal inlet 27, and thereby seals the distal opening of the guide 12 in fluid communication with the laryngeal inlet. The side portions 37 and 38 (shown in FIG. 4) pinch the sides of the epiglottis 25, which also tends to lift the epiglottis 25 from the laryngeal inlet 27.

If necessary, the guide cap 91 can be removed and an endoscope probe can be inserted through the proximal end of the guide 12 to enable the physician to view the insertion process and verify that the laryngeal mask 30 is correctly positioned.

Optionally, a syringe 55 containing a local anesthetic (e.g., lidocaine or xylocaine) can be connected to the luer connector on the guide cap 91 at the proximal end of the guide 12 to squirt anesthetic as the guide 12 is inserted through the patient's mouth and into the laryngopharynx 21, as shown in FIG. 16. If squirted with sufficient force, the anesthetic can be carried as far as the larynx 24 to deaden any discomfort associated with insertion of the laryngeal mask airway 10 and endotracheal tube 40.

During and after insertion of the guide 12, the patient can be resuscitated by supplying air/oxygen through the ventilation port 16. For example, the flow of air can be supplied by a resuscitation bag attached to the ventilation port 16 that is manually squeezed periodically to simulate natural breathing. Alternatively, a resuscitation attachment (such as shown in FIGS. 5–7) can be removably attached to the ventilation port 16 to enable a healthcare provider to directly resuscitate the patient.

Figure 17:
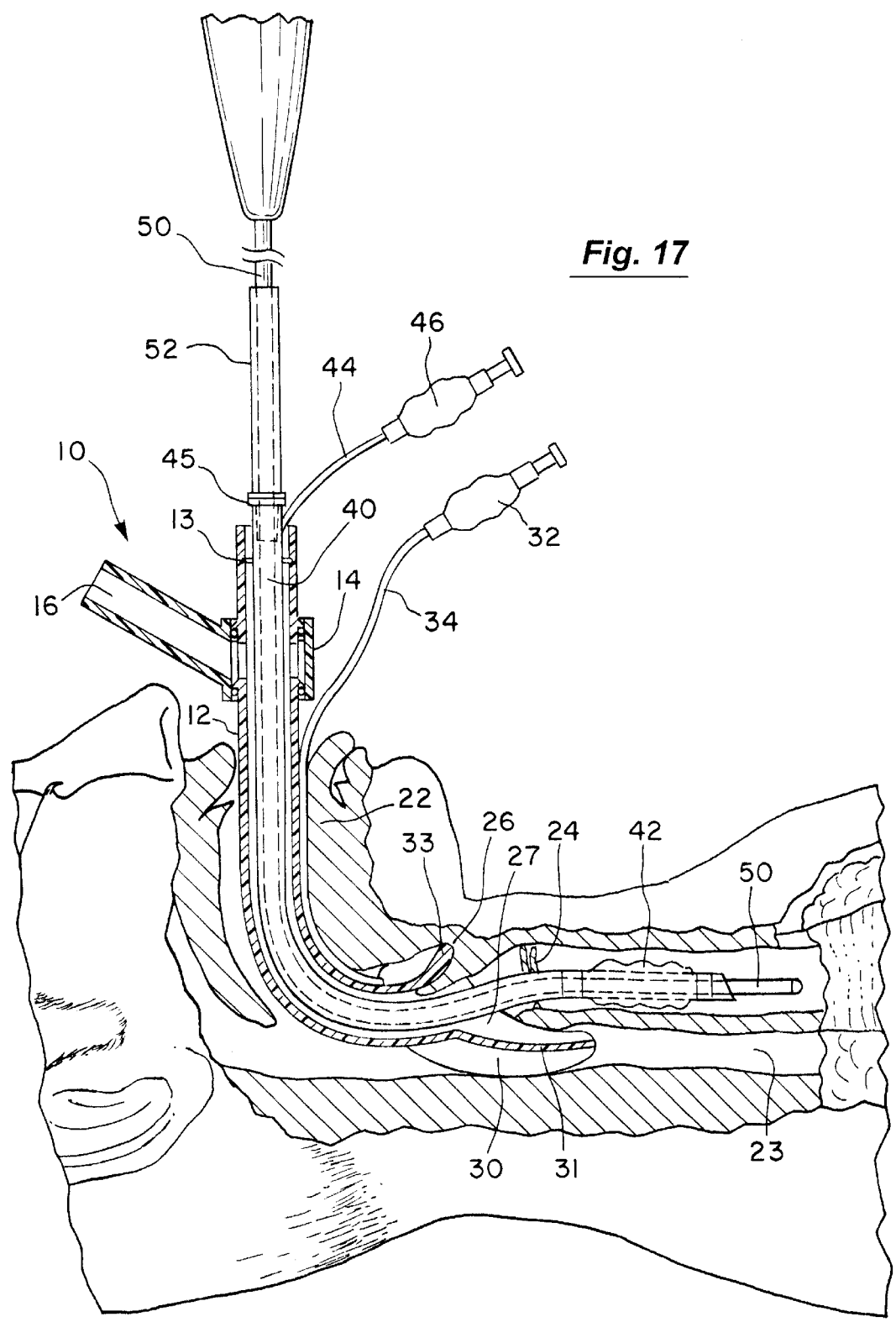
FIG. 17 is a cross-sectional view of the laryngeal mask airway 10 and the patient's airway corresponding to FIGS. 14–16 after an endotracheal tube 40 has been inserted through the laryngeal mask airway 10.

After the patient's condition has been stabilized to some degree during initial resuscitation, an endotracheal tube 40 is inserted over the distal end of an endoscope probe 50. The guide cap 91 is removed from the proximal end of the guide 12. Resuscitation, oxygenation, or artificial ventilation continue without interruption while the endoscope probe 50 and endotracheal tube 40 are advanced along the guide 12 and through the laryngeal mask 30 to a position within the trachea past the larynx 24. FIG. 17 is a cross-sectional view of the laryngeal mask airway 10 during insertion of the endotracheal tube 40 and endoscope probe 50.

The seal ring 13 within the proximal end of the guide 12 has an inside diameter that is only slightly larger than the outside diameter of the endotracheal tube 40. This maintains a sufficiently tight fit around the endotracheal tube 40 to prevent the escape of gas through the seal. However, air/oxygen flows freely through the space between the endotracheal tube 40 and the surrounding guide 12 to maintain patient respiration.

Optionally, a removable cap 45 can be inserted into the proximal end of the endotracheal tube 40 and a stabilizer tube 52 can be attached to the endoscope probe 50, as shown in FIG. 17, to assist in advancing the endotracheal tube 40 along the guide 12. In the preferred embodiment, the stabilizer 52 is a flexible plastic tube having a C-shaped cross-section, as shown in FIG. 22, that can be readily clipped over the fiber optic probe 50 at any desired location along its length. The inside diameter of the stabilizer 52 should be selected to provide a snug, frictional fit against the exterior of the endoscope probe 50 so that the stabilizer 52 will not readily slide after it has been attached to the fiber optic probe 50. The stabilizer 52 can also be readily removed from the endoscope probe 50 by the healthcare provider for cleaning or to adjust its location on the probe 50. The stabilizer 52 should have outside dimensions sufficiently large to push the endotracheal tube 40 forward as the fiber optic probe 50 is advanced by the healthcare provider.

The proximal end of the endotracheal tube 40 can be fitted with a removable cap 45 shown in FIG. 23. This cap 45 has outside dimensions selected so that it can be inserted snugly into the proximal opening of the endotracheal tube 40 and yet is sufficiently small to pass through the guide 12, if necessary. A central passageway extends axially through the endotracheal tube cap 45 to receive the endoscope 50. The endoscope probe 50 passes freely through the cap 45. However, the cap passageway has an inside diameter smaller than the stabilizer 52, so that the stabilizer 52 will abut and push against the proximal end of the endotracheal tube 40 as the fiber optic probe 50 is advanced by the healthcare provider. This approach enables the endotracheal tube 40 and endoscope probe 50 to be advanced along the guide 12 and patient's airway as a single assembly.

The shape of the guide 12, the support member 31, and laryngeal mask 30 tend to align the distal opening of the guide 12 with the larynx 24 so that the endoscope probe 50 and endotracheal tube 40 will pass through the opening between the vocal cords. However, after emerging from the distal end of the guide 12, the direction of the distal tip of the endoscope probe 50 can be controlled by the physician. This allows the physician to carefully guide the endoscope probe 50 and endotracheal tube 40 to a position past the larynx 24 while resuscitation continues. Many conventional endoscopes include a suction channel extending the length of the fiber optic probe to its distal tip. This feature can be used to suction mucus or other secretions from the patient's airway as the endoscope/endotracheal tube assembly is inserted. Alternatively, an endoscope 50 may not be needed at all due to the anatomical alignment provided by the laryngeal mask 30, which permits "blind" intubation of the patient. In any event, the patient is being ventilated throughout the intubation process, so the normal risks associated with intubation are not as serious if delays are encountered in completing the intubation process using the present invention.

Figure 18:
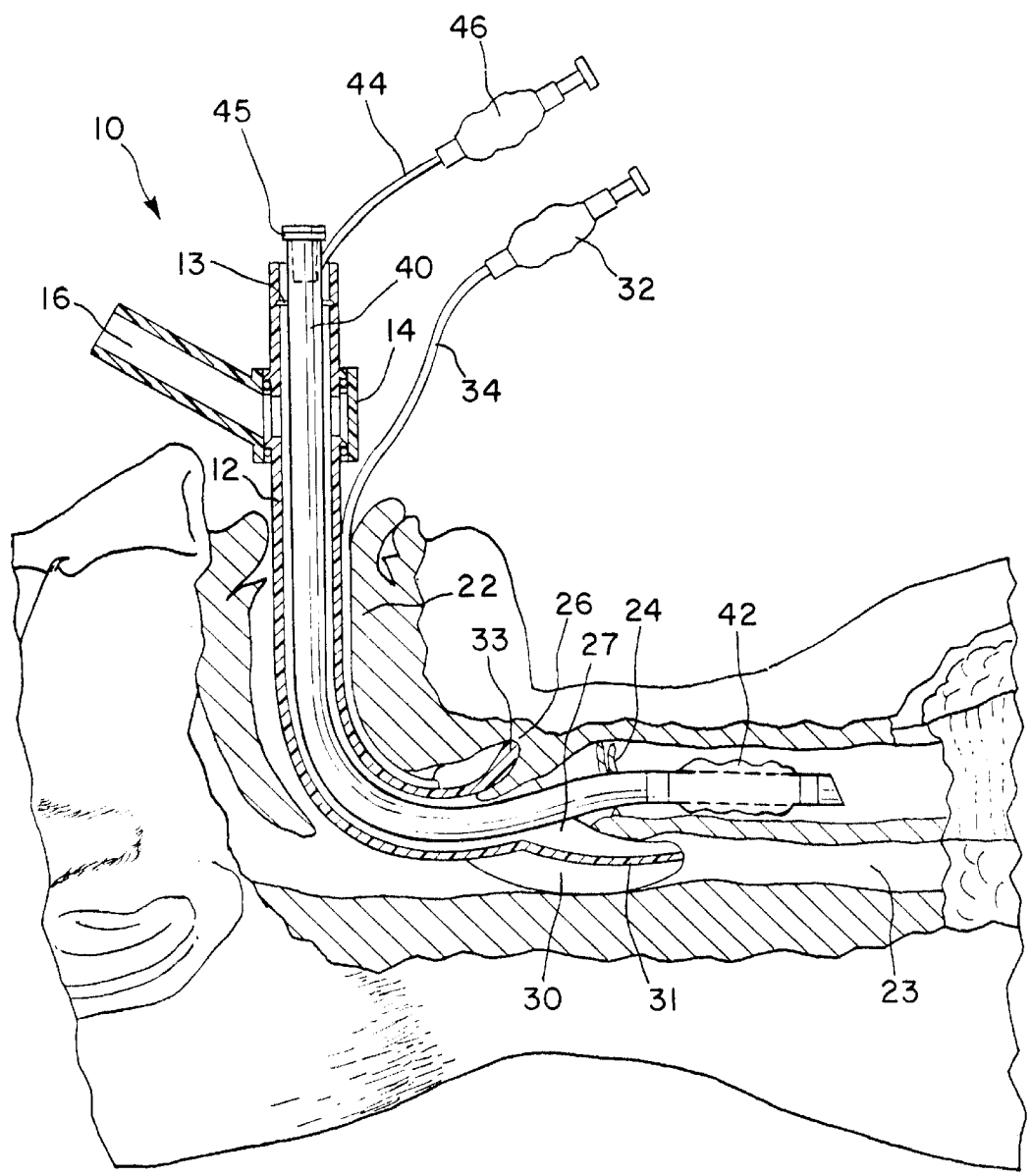
FIG. 18 is a cross-sectional view of the laryngeal mask airway 10 and the patient's airway corresponding to FIGS. 14–17 after the endoscope probe 50 has been withdrawn from within the endotracheal tube 40.
Figure 19:
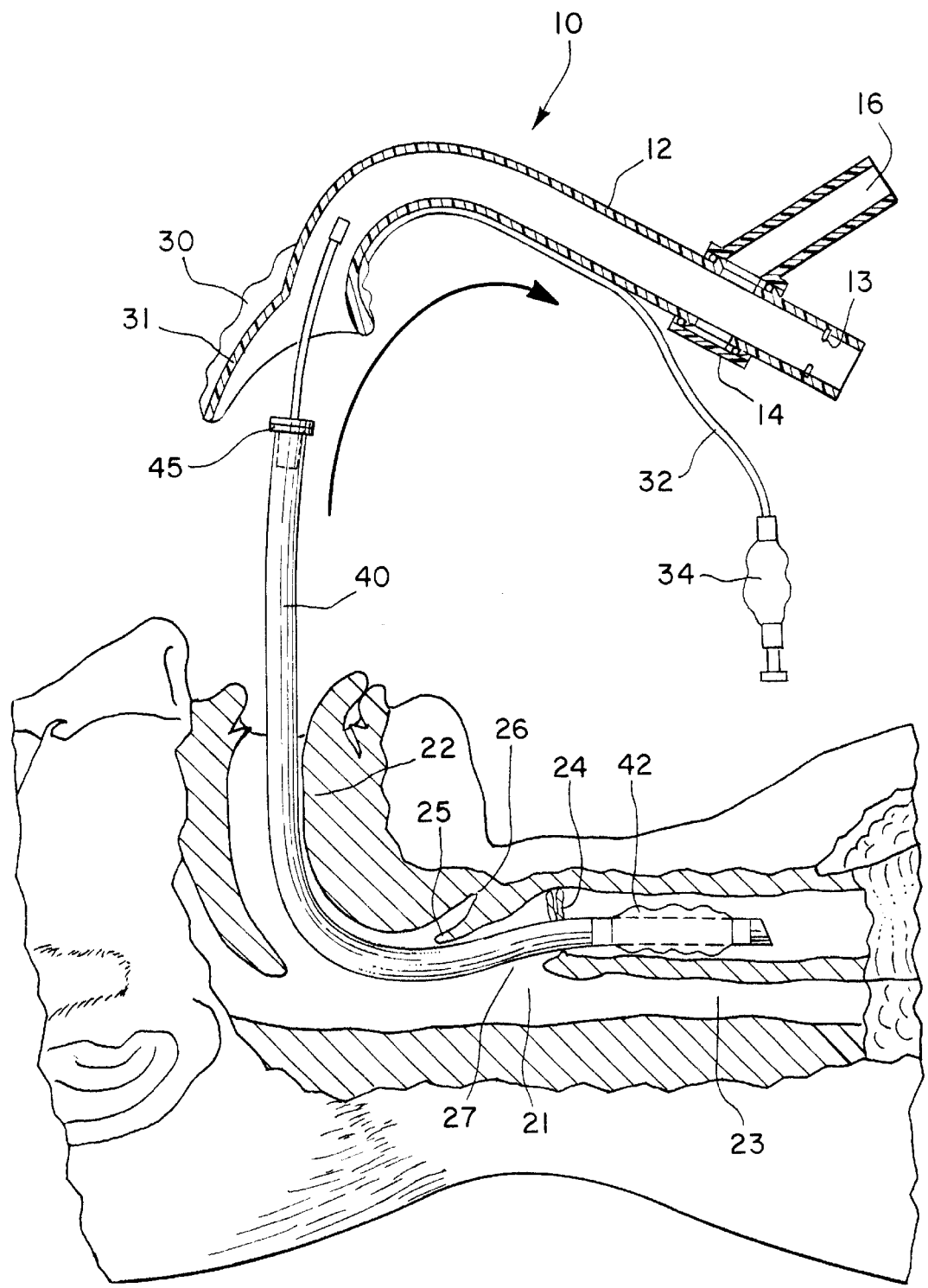
FIG. 19 is a cross-sectional view of the laryngeal mask airway 10 and the patient's airway corresponding to FIGS. 14–18 after the mask 30 has been deflated and the laryngeal mask airway 10 has been removed, leaving the endotracheal tube 40 in place in the patient's airway.

In one methodology, the endoscope probe 50 is then removed from within the endotracheal tube 40, as shown in FIG. 18. The laryngeal mask 30 is deflated and the guide 12 is removed while leaving the endotracheal tube 40 in place within the trachea, as illustrated in FIG. 19. Alternatively, the guide 12 can be left in place to serve as an oral airway and to protect the endotracheal tube 40 from being bitten by the patient's teeth. However, the laryngeal mask 30 should be deflated if the device is to be left in place in the patient's airway for an extended period time to minimize damage to the mucous lining.

Figure 20:
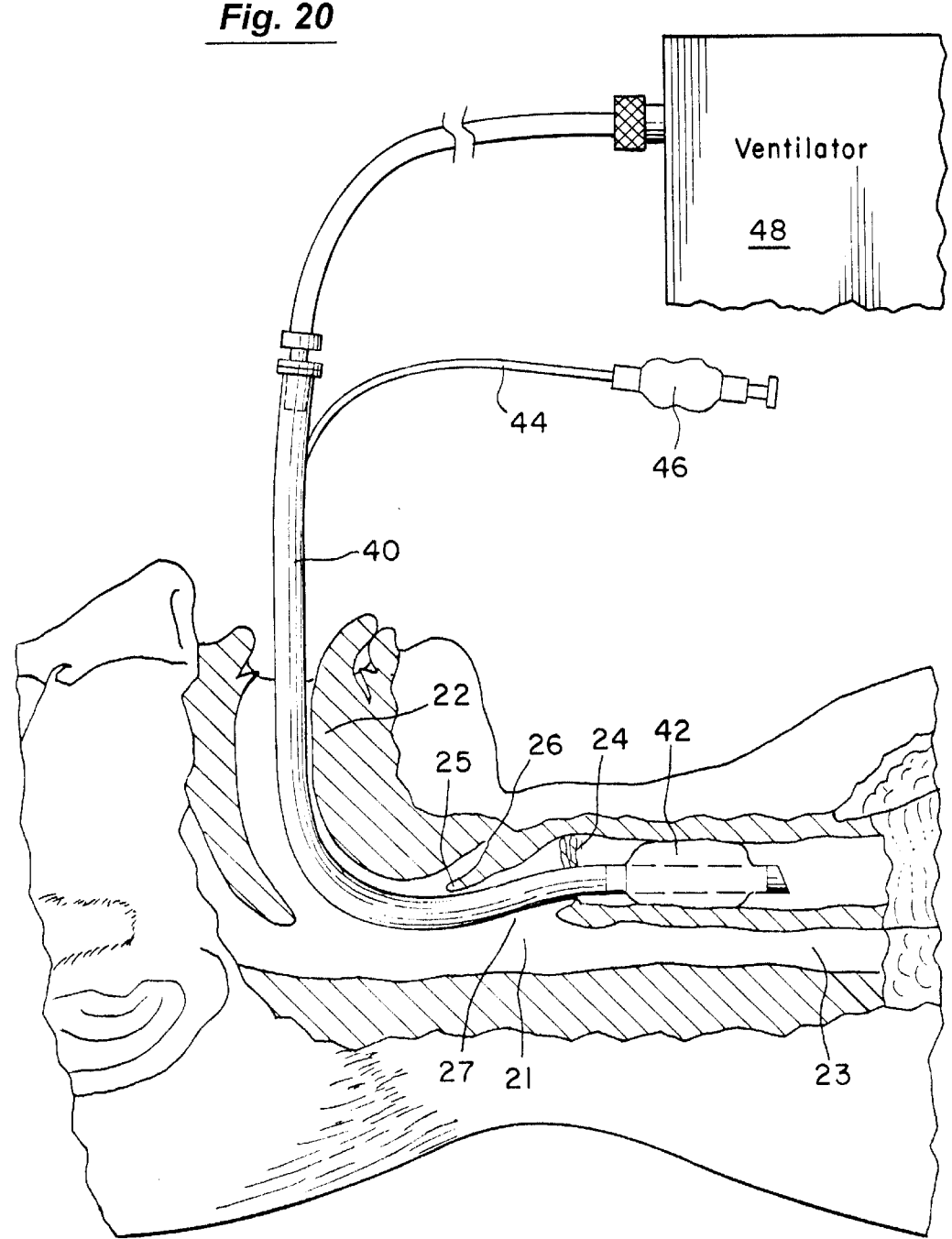
FIG. 20 is a cross-sectional view of the patient's airway corresponding to FIGS. 14–19 after the cuff 42 of the endotracheal tube 40 has been inflated and the patient has been connected to a ventilator 48.

The cuff 42 on the endotracheal tube 40 is then inflated via an inflation tube 44 and air valve 46. Finally, a ventilator 48 is connected to the proximal end of the endotracheal tube 40 to ventilate the patient, as shown in FIG. 20. Alternatively, the patient can be manually ventilated by connecting a resuscitation bag to the proximal end of the endotracheal tube 40.

Figure 21:
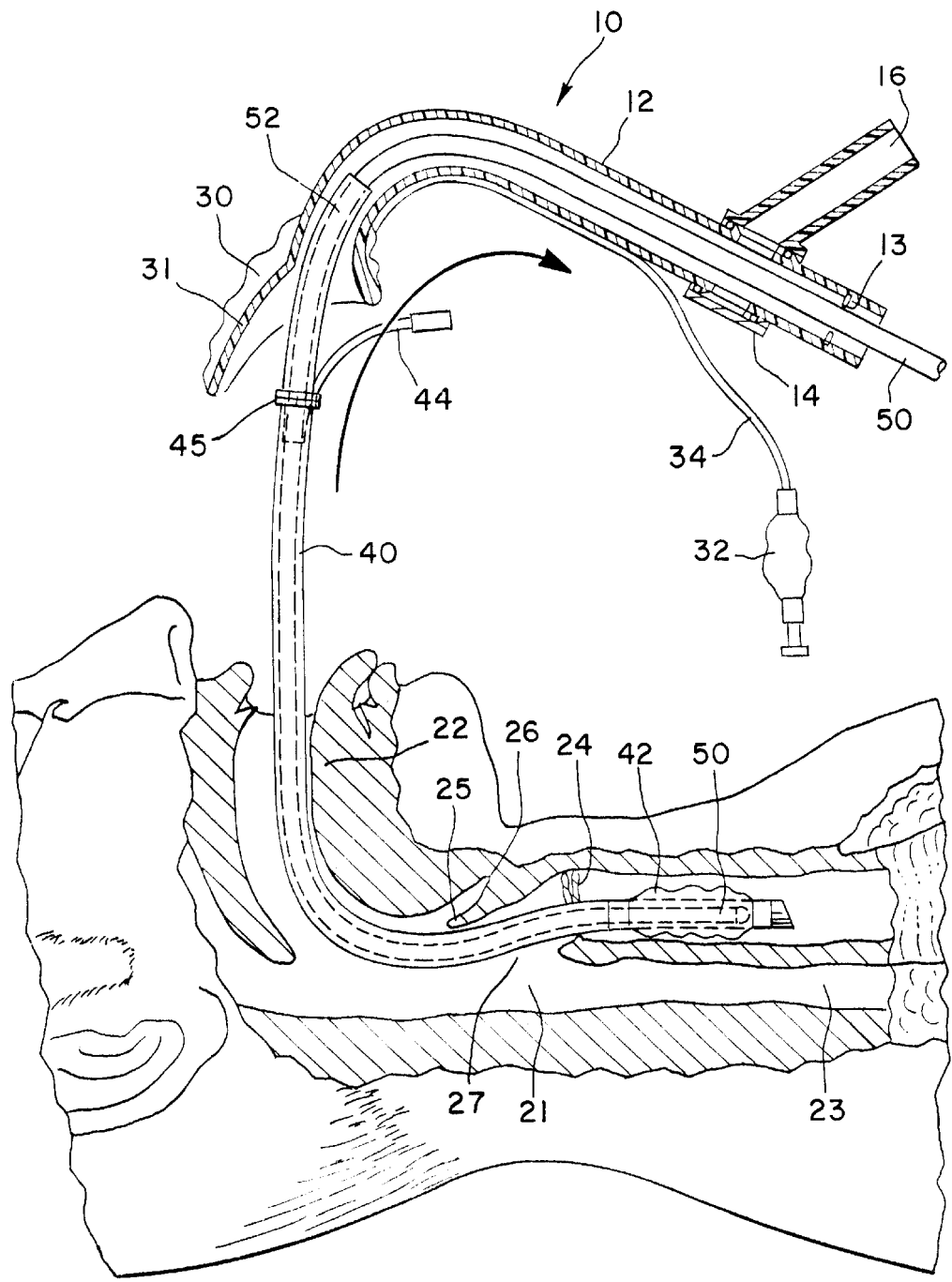
FIG. 21 is a cross-sectional view of the patient's airway corresponding to FIG. 14–20 in an alternative methodology in which the laryngeal mask airway 10 is withdrawn over the endoscope probe 50 while leaving the endotracheal tube 40 in place in the patient's airway.

FIG. 21 depicts an alternative methodology in which the laryngeal mask airway 10 is withdrawn over the endoscope probe 50 while leaving the endotracheal tube 40 in place in the patient's airway. In this methodology, after the endotracheal tube 40 has been moved into position with its distal end in the trachea as illustrated in 17, the laryngeal mask 30 is deflated and the guide 12 is removed over the proximal end of the endotracheal tube 40 while leaving the endotracheal tube 40 and fiber optic probe 50 in place. Before removing the guide 12, the healthcare provider may wish to slide the stabilizer 52 a few centimeters toward the distal end of the fiber optic probe 50. This allows the endoscope 50 to be pulled back relative to the endotracheal tube 40, so that the distal tip of the endoscope 50 is located within the distal end of the endotracheal tube 40 and offers a view of both the endotracheal tube's distal tip and the patient's trachea. This enables the healthcare provider to monitor the position of the endotracheal tube 40 relative to the trachea as the guide 12 is removed, as described above.

The fiber optic probe 50 is then withdrawn from within the endotracheal tube 40 and the endotracheal tube cap 45 is removed if one is present. Finally, the patient can be ventilated via a conventional ventilator 48 connected to the endotracheal tube 40, as shown in FIG. 20.

Figure 24:
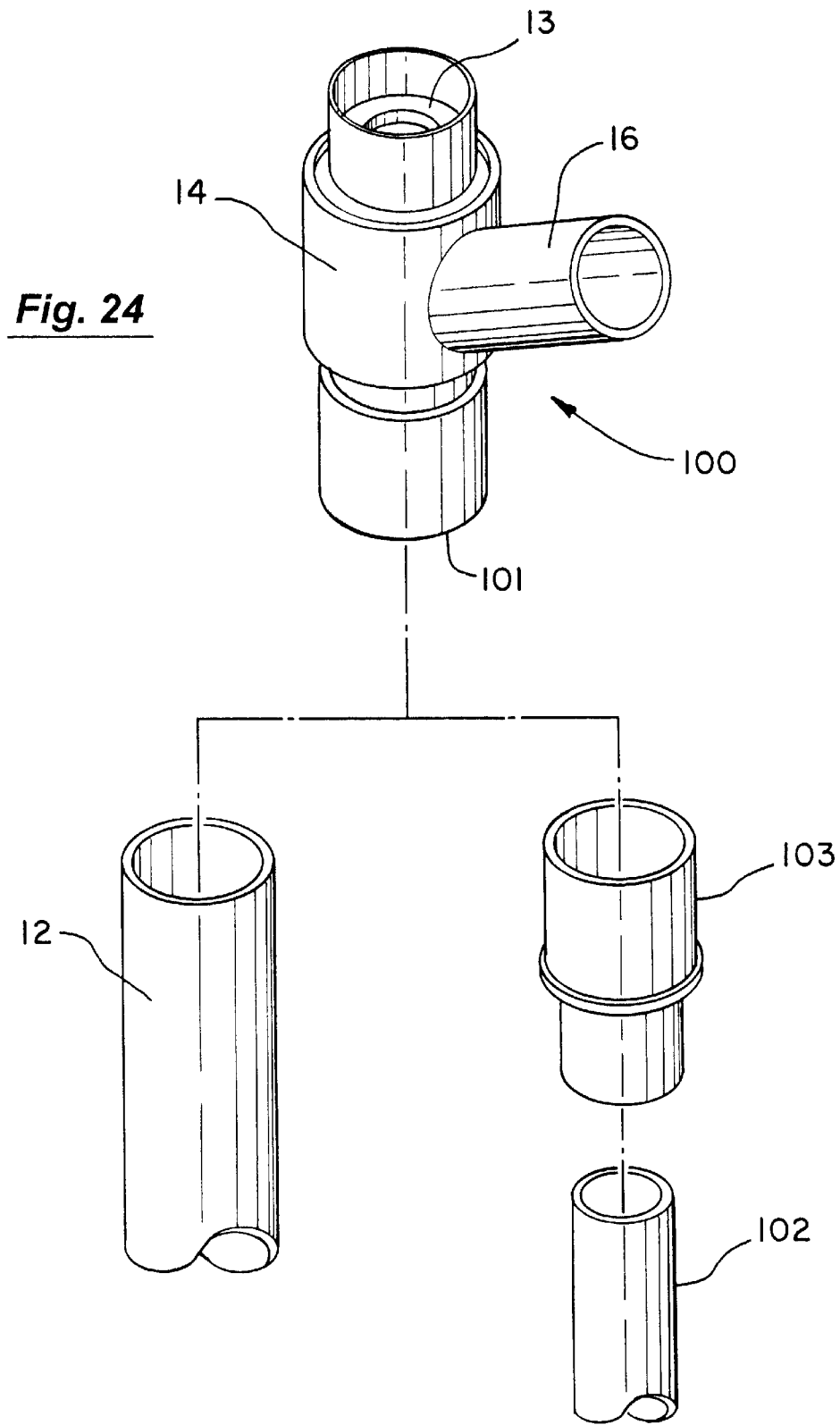
FIG. 24 is an exploded perspective view of an embodiment of the present invention in which a separate ventilation attachment 100 can either be used in combination with a guide 12 or a conventional laryngeal mask airway 102.
Figure 25:
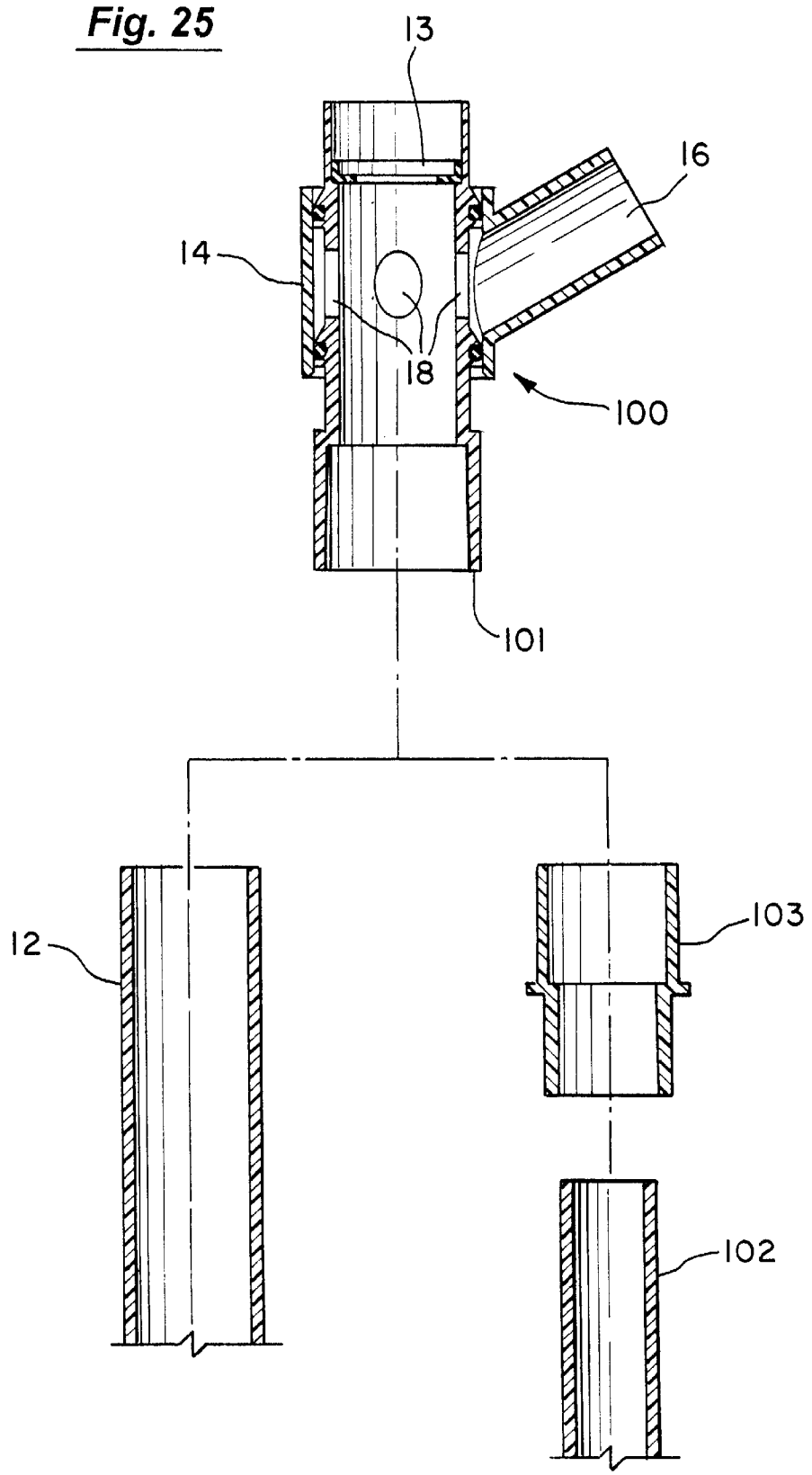
FIG. 25 is an exploded cross-sectional view corresponding to FIG. 24.

Ventilation Attachment. FIG. 24 is an exploded perspective view of an embodiment using a separate ventilation attachment 100 with a rotatable ventilation port 16. FIG. 25 is an exploded cross-sectional view corresponding to FIG. 24. The ventilation attachment 100 provides the same functionality as the proximal portion of the laryngeal mask airway 10 in the previous embodiments. The ventilation attachment 100 has a passageway with a diameter large enough to allow an endotracheal tube to pass through the ventilation attachment 100. A ventilation port 16 allows a flow of air/oxygen to be supplied through the guide 12 around the periphery of the endotracheal tube and into the patient's lungs during insertion of the endotracheal tube, as previously discussed. A seal ring 13 in the passageway forms a seal around the endotracheal tube as the endotracheal tube is inserted through the ventilation attachment 100 and along the guide 12. In other words, the seal ring 13 provides a seal around the endotracheal tube as it is inserted through the ventilation attachment 100 to prevent air/oxygen from escaping from within the passageway while the patient is being ventilated. But, the seal ring 13 allows the endotracheal tube to be advanced through the ventilation attachment 100 and guide 12 with minimal resistance.

The ventilation attachment 100 can either be used in combination with a J-shaped guide 12 similar to that shown in the previous embodiments, or with a conventional laryngeal mask airway 102. If used in combination with the J-shaped guide 12, the cuff 101 at the lower end of the ventilation attachment 100 fits directly over the proximal opening of the guide 12. In contrast, conventional laryngeal mask airways 102 typically have a standard 15 mm respirator connector (not shown) at their proximal end, which may or may not be removable depending on the specific model involved. If possible, the respirator connector should be removed from the end of the laryngeal mask airway 102, as illustrated in FIG. 24 to provide a larger diameter for subsequent insertion of an endotracheal tube. If the respirator connector cannot be removed from the end of the laryngeal mask airway 102, the ventilation attachment 100 can be attached over the respirator connector. If necessary, a tubular adapter 103 can be inserted between the cuff 101 of the ventilation attachment 100 and the upper end of the guide to accommodate any change in diameter between the cuff 101 and the end of the guide.

It should be understood that the term "guide" encompasses any type of guide or laryngeal mask airway for the purposes of this invention. In either case, the cuff 101 serves to coaxially align the passageway of the ventilation attachment 100 with the guide, so that an endotracheal tube can be inserted through both.

Figure 26:
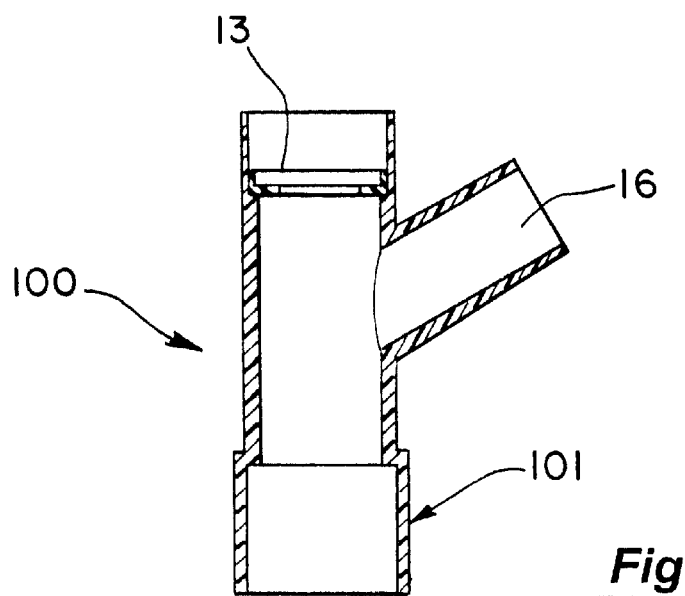
FIG. 26 is a cross-sectional view of a ventilation attachment 100 having a fixed ventilation port 16.

The embodiment illustrated in FIGS. 24–25 includes a rotatable collar 14 so that the ventilation port 16 can be rotated to any desired orientation relative to the longitudinal axis of the guide. In contrast, FIG. 26 is a cross-sectional view of an embodiment of the ventilation attachment 100 having a fixed ventilation port 16. The orientation of the ventilation port 16 can be adjusted by rotating the cuff 101 (and therefore the entire ventilation attachment 100 including the ventilation port 16) relative to the guide.

Figure 27:
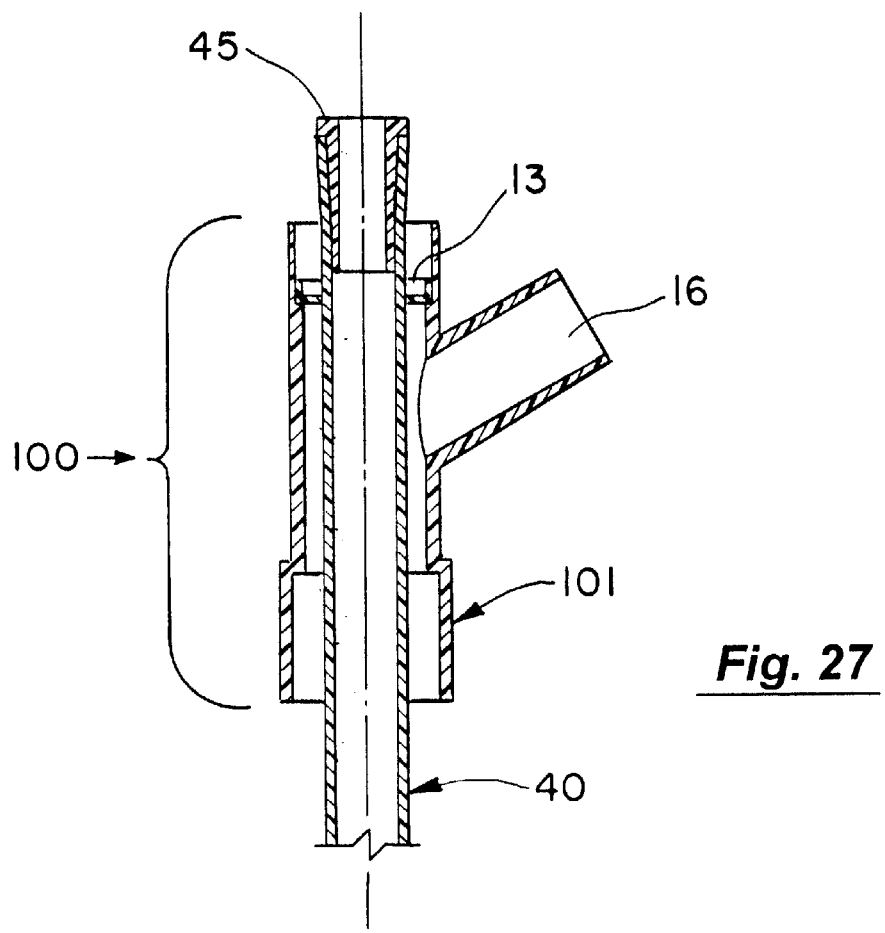
FIG. 27 is a cross-sectional view corresponding to FIG. 26 showing insertion of an endotracheal tube 40 through the ventilation attachment 100.

The embodiments in FIG. 24–26 are intended for use primarily in a clinical setting (e.g., while administering anesthesia in an operating room). The vast majority of surgical patients do not encounter complications that would require intubation with an endotracheal tube. For these patients, a laryngeal mask airway 102 by itself is sufficient for administering anesthesia. If the patient gets into trouble requiring intubation, the ventilation attachment 100 can be quickly added to the proximal end of the laryngeal mask airway 102 as shown in FIGS. 24 and 25, and an endotracheal tube 40 can then be inserted through the ventilation attachment 100 as shown in FIG. 27 and described above. The embodiment of the ventilation attachment 100 depicted in FIG. 26, in particular, would be simpler to manufacture and more cost effective for this type of infrequent use.

Figure 28:
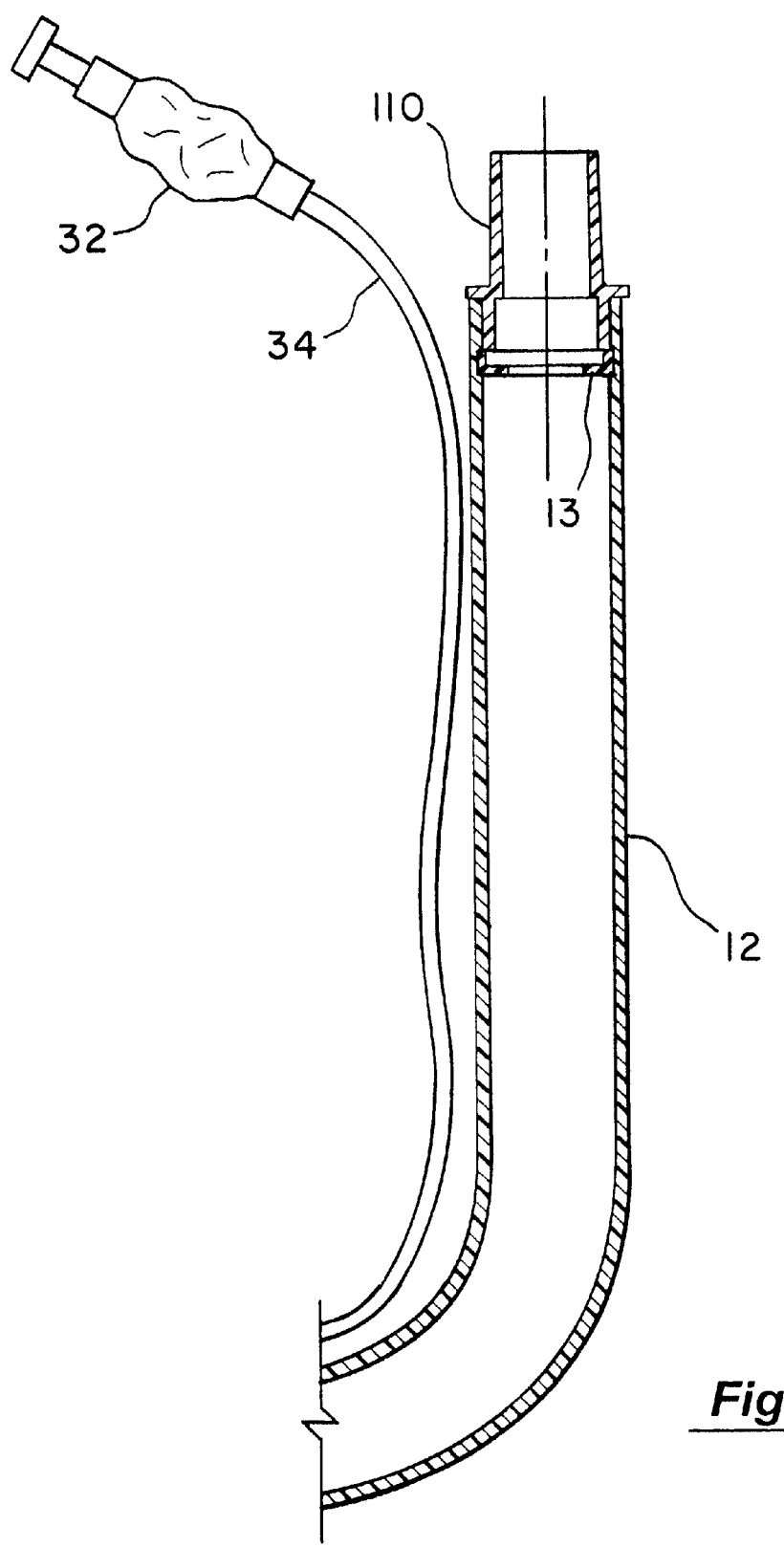
FIG. 28 is a cross-sectional view of a laryngeal mask airway 10 with a removable ventilator connector 110 attached to its proximal end in place of the ventilation attachment 100.

FIG. 28 is a cross-sectional view of a guide 12 with a removable ventilator connector 110 attached to its proximal end in place of the ventilation attachment 100. The ventilation connector 110 has a standard 15 mm diameter that allows the patient to be connected to a conventional ventilator. If the patient encountered difficulties requiring intubation, the ventilator connector 110 can be quickly removed from the guide 12 and replaced with the ventilation attachment 100 as shown in FIGS. 24–25.

The above disclosure sets forth a number of embodiments of the present invention. Other arrangements or embodiments, not precisely set forth, could be practiced under the teachings of the present invention and as set forth in the following claims.

I claim:

1. A laryngeal mask airway comprising:
   a curved tubular guide for insertion through a patient's mouth and into the patient's airway and allowing insertion of an endotracheal tube through the guide, said guide having a distal opening defining an axis for advancing an endotracheal tube beyond the guide, and a proximal opening remaining outside the patient's mouth after insertion of the guide;
   a support member extending from the outer curvature of the distal opening of the guide in a direction substantially parallel to, and offset from the axis of the distal opening of the guide;
   a laryngeal mask surrounding the support member and distal opening of the guide to substantially seal the patient's glottis about the distal opening of the guide and axially align the distal opening of the guide with the patient's glottis on end as the guide is inserted alone the patient's airway, thereby enabling an endotracheal tube to be advanced axially from the distal opening of the guide into the patient's trachea; and
   a ventilation attachment removably attachable to the proximal opening of the guide, having a ventilation port to supply a flow of air/oxygen through the guide into the patient's lungs during insertion of an endotracheal tube along the guide.

2. The laryngeal mask airway of claim 1 wherein the ventilation attachment further comprises:
   a passageway aligned with the guide allowing insertion of an endotracheal tube; and
   a ventilation port allowing air/oxygen to be supplied through the passageway and guide as the endotracheal tube is inserted.

3. The laryngeal mask airway of claim 2 wherein the ventilation attachment further comprises a seal ring within the passageway providing a seal around the endotracheal tube as the endotracheal tube is inserted through the ventilation attachment to prevent air/oxygen from escaping from within the passageway but allowing the endotracheal tube to be advanced through the ventilation attachment.

4. The laryngeal mask airway of claim 2 wherein the ventilation attachment further comprises a rotatable collar surrounding the passageway allowing the ventilation port to be rotated to any desired orientation about the ventilation attachment.

5. The laryngeal mask airway of claim 1 wherein the laryngeal mask further comprises:
   a lower portion shaped to substantially block the patient's esophagus below the patient's glottis; and
   an upper portion surrounding the distal opening of the guide and substantially filling the patient's laryngopharynx adjacent to the glottis, wherein the laryngeal mask directs the guide along the patient's airway so that the distal opening of the guide abuts the patient's glottis.

6. The laryngeal mask airway of claim 1 wherein the guide further comprises a distal tip having a protrusion from the inner curvature of guide to push against the patient's vallecula and thereby lift the patient's epiglottis from the glottis.

7. The laryngeal mask airway of claim 1 wherein the laryngeal mask further comprises opposing side portions to pinch the patient's epiglottis between the side portions of the laryngeal mask as the guide is inserted into the patient's laryngopharynx to thereby lift the epiglottis from the glottis.

8. The laryngeal mask airway of claim 1 wherein the laryngeal mask is inflatable.

9. The laryngeal mask airway of claim 1 wherein the laryngeal mask comprises a soft, resilient material.

10. A laryngeal mask airway comprising:
   a curved tubular guide for insertion through a patient's mouth and into the patient's airway to allow insertion of an endotracheal tube along the guide and through the patient's larynx, said guide having a distal opening defining an axis for advancing an endotracheal tube beyond the guide, and a proximal opening remaining outside the patient's mouth after insertion of the guide; and
   a laryngeal mask surrounding the distal opening of the guide to substantially seal the patient's glottis about the distal opening of the guide and substantially seal the patient's esophageal opening, said laryngeal mask having:
      (a) a support member extending from the outer curvature at the distal end the guide in a direction substantially parallel to and offset from the axis of the distal opening of the guide, and having a tip extending into the patient's esophagus;
      (b) a protrusion from the inner curvature at the distal end of the guide to push against the patient's vallecula and thereby lift the patient's epiglottis from the patient's glottis as the guide is inserted into the patient's laryngopharynx;
      (c) a lower portion extending from the support member that is shaped to substantially block the patient's esophagus below the patient's glottis and align the distal opening of the guide with the patient's glottis as the guide is advanced along the patient's airway;
      (d) an upper portion extending from the support member and surrounding the distal opening of the guide to substantially fill the patient's laryngopharynx adjacent to the patient's glottis; and
      (e) opposing side portions to pinch the patient's epiglottis and thereby lift the epiglottis from the glottis, so that the distal opening of the guide is axially aligned with and abuts the patient's glottis on end as the guide is advanced along the patient's airway and is sealed in fluid communication with the patient's glottis, thereby enabling an endotracheal tube to be advanced axially from the distal opening of the guide into the patient's trachea; and
   a ventilation attachment removably attachable to the proximal opening of the guide, having a ventilation port to supply air/oxygen through the guide during insertion of an endotracheal tube along the guide.

11. The laryngeal mask airway of claim 10 wherein the ventilation attachment further comprises:
   a passageway aligned with the guide allowing insertion of an endotracheal tube; and
   a ventilation port allowing air/oxygen to be supplied through the passageway and guide as the endotracheal tube is inserted.

12. The laryngeal mask airway of claim 11 wherein the ventilation attachment further comprises a rotatable collar surrounding the passageway allowing the ventilation port to be rotated to any desired orientation about the ventilation attachment.

13. The laryngeal mask airway of claim 11 wherein the ventilation attachment further comprises a seal ring within the passageway providing a seal around the endotracheal tube as the endotracheal tube is inserted through the ventilation attachment to prevent air/oxygen from escaping from within the passageway but allowing the endotracheal tube to be advanced through the ventilation attachment.

14. The laryngeal mask airway of claim 10 wherein the laryngeal mask is inflatable.

15. A laryngeal mask airway comprising:
   a curved tubular guide for insertion through a patient's mouth and into the patient's airway and allowing insertion of an endotracheal tube through the guide, said guide having a distal opening defining an axis for advancing an endotracheal tube beyond the guide, and a proximal opening remaining outside the patient's mouth after insertion of the guide;
   a support member extending from the outside curvature of the guide at the distal opening of the guide in a direction substantially parallel to, and offset from the axis of the distal opening of the guide;
   a laryngeal mask surrounding the support member and distal opening of the guide to substantially seal the patient's glottis about the distal opening of the guide and axially align the distal opening of the guide with the patient's glottis on end as the guide is inserted along the patient's airway, thereby enabling an endotracheal tube to be advanced axially from the distal opening of the guide into the patient's trachea; and
   a ventilation attachment having:
      (a) a passageway aligned with the guide allowing insertion of an endotracheal tube;
      (b) a ventilation port allowing air/oxygen to be supplied to the patient through the passageway and guide as the endotracheal tube is inserted through the passageway and guide; and
      (c) a cuff removably attaching the ventilation attachment to the proximal opening of the guide.

16. The laryngeal mask airway of claim 15 wherein the ventilation attachment further comprises a seal ring within the passageway providing a seal around the endotracheal tube as the endotracheal tube is inserted through the ventilation attachment to prevent air/oxygen from escaping from within the passageway but allowing the endotracheal tube to be advanced through the ventilation attachment.

17. The laryngeal mask airway of claim 15 wherein the ventilation attachment further comprises a rotatable collar surrounding the passageway allowing the ventilation port to be rotated to any desired orientation about the ventilation attachment.

18. The laryngeal mask airway of claim 15 wherein the laryngeal mask further comprises:
   a lower portion shaped to substantially block the patient's esophagus below the patient's glottis; and
   an upper portion surrounding the distal opening of the guide and substantially filling the patient's laryngopharynx adjacent to the patient's glottis, wherein the laryngeal mask directs the guide along the patient's airway so that the distal opening of the guide abuts the patient's glottis.

19. The laryngeal mask airway of claim 15 wherein the guide further comprises a distal tip having a protrusion extending from the inner curvature at the distal tip to push against the patient's vallecula and thereby lift the patient's epiglottis from the glottis.

20. The laryngeal mask airway of claim 15 wherein the laryngeal mask further comprises opposing side portions to pinch the patient's epiglottis between the side portions of the laryngeal mask as the guide is inserted into the patient's laryngopharynx to thereby lift the epiglottis from the glottis.

* * * * *